(12) United States Patent
Sullivan et al.

(10) Patent No.: US 11,021,617 B2
(45) Date of Patent: Jun. 1, 2021

(54) POLYMERS INCLUDING ONE OR MORE 1,1-DISUBSTITUTED ALKENE COMPOUNDS AND POLYMER COMPOSITIONS THEREOF

(71) Applicant: Sirrus, Inc., Loveland, OH (US)

(72) Inventors: Jeffrey M. Sullivan, Cincinnati, OH (US); Aniruddha Palsule, Cincinnati, OH (US); Alexander R. Holzer, Cincinnati, OH (US); Peter Rulon Stevenson, Salt Lake City, UT (US); Kshitij Kishen Parab, Loveland, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 16/381,249

(22) Filed: Apr. 11, 2019

(65) Prior Publication Data

US 2019/0263955 A1 Aug. 29, 2019

Related U.S. Application Data

(60) Division of application No. 15/509,403, filed as application No. PCT/US2015/048846 on Sep. 8, (Continued)

(51) Int. Cl.
*C08F 220/10* (2006.01)
*C08F 222/10* (2006.01)
(Continued)

(52) U.S. Cl.
CPC ............... *C09D 7/45* (2018.01); *B01J 19/10* (2013.01); *B01J 19/18* (2013.01); *C07C 69/38* (2013.01);
(Continued)

(58) Field of Classification Search
None
See application file for complete search history.

(56) References Cited

U.S. PATENT DOCUMENTS

| 2,212,506 A | 8/1940 | Bachman |
| 2,230,033 A | 1/1941 | Hackett |

(Continued)

FOREIGN PATENT DOCUMENTS

| CN | 102901754 A | 1/2013 |
| DE | 19508049 A1 | 9/1996 |

(Continued)

OTHER PUBLICATIONS

Philip Klemarczyk, Polymer 1998, 39(1), 173-181.*
(Continued)

*Primary Examiner* — Vu A Nguyen
(74) *Attorney, Agent, or Firm* — Young Basile Hanlon & MacFarlane, P.C.

(57) ABSTRACT

The disclosure relates to polymers including one or more 1,1-disubstitued alkene monomers. By employing a plurality of monomers and/or tailored chain structure, polymers having improved combinations of properties are achieved. The polymer may be a copolymer, preferably including two or more 1,1-disubstituted alkene monomers. The polymer may be a homopolymer having a tailored chain structure.

12 Claims, 13 Drawing Sheets

NMR spectrogram showing presence of unreacted monomer

NMR spectrogram after polymerization showing ≈100% monomer conversion.

Related U.S. Application Data 2015, now Pat. No. 10,308,802, which is a continuation-in-part of application No. 14/810,741, filed on Jul. 28, 2015, now Pat. No. 9,279,022, which is a continuation-in-part of application No. 14/789,178, filed on Jul. 1, 2015, now Pat. No. 9,249,265.

(60) Provisional application No. 62/186,479, filed on Jun. 30, 2015, provisional application No. 62/182,076, filed on Jun. 19, 2015, provisional application No. 62/047,328, filed on Sep. 8, 2014, provisional application No. 62/047,283, filed on Sep. 8, 2014.

(51) Int. Cl.
| | |
|---|---|
| *C08F 267/06* | (2006.01) |
| *C08F 293/00* | (2006.01) |
| *C09D 7/45* | (2018.01) |
| *C08J 3/07* | (2006.01) |
| *C08F 22/10* | (2006.01) |
| *B01J 19/10* | (2006.01) |
| *B01J 19/18* | (2006.01) |
| *C07C 69/38* | (2006.01) |
| *C08F 2/22* | (2006.01) |
| *C08F 222/14* | (2006.01) |
| *C08L 33/04* | (2006.01) |
| *C08F 2/30* | (2006.01) |
| *C08F 2/26* | (2006.01) |
| *C08F 122/14* | (2006.01) |
| *C09D 7/65* | (2018.01) |
| *C09D 135/02* | (2006.01) |
| *C09J 11/06* | (2006.01) |
| *C09J 11/08* | (2006.01) |
| *C09J 135/02* | (2006.01) |
| *C08K 5/103* | (2006.01) |
| *C08K 5/1535* | (2006.01) |
| *C08K 5/42* | (2006.01) |

(52) U.S. Cl.
CPC .............. *C08F 2/22* (2013.01); *C08F 2/26* (2013.01); *C08F 2/30* (2013.01); *C08F 22/10* (2013.01); *C08F 122/14* (2013.01); *C08F 222/10* (2013.01); *C08F 222/14* (2013.01); *C08F 267/06* (2013.01); *C08F 293/00* (2013.01); *C08J 3/07* (2013.01); *C08L 33/04* (2013.01); *C09D 7/65* (2018.01); *C09D 135/02* (2013.01); *C09J 11/06* (2013.01); *C09J 11/08* (2013.01); *C09J 135/02* (2013.01); *C08K 5/103* (2013.01); *C08K 5/1535* (2013.01); *C08K 5/42* (2013.01)

(56) References Cited

U.S. PATENT DOCUMENTS

| | | |
|---|---|---|
| 2,245,567 A | 6/1941 | Brant et al. |
| 2,277,479 A | 3/1942 | D'Aiello |
| 2,313,501 A | 3/1943 | Bachman |
| 2,330,033 A * | 9/1943 | D Alelio .............. C07C 69/593 560/203 |
| 2,403,791 A | 7/1946 | D'Aiello |
| 2,569,797 A | 10/1951 | Knock |
| 3,042,710 A | 7/1962 | Dickstein et al. |
| 3,197,318 A | 7/1965 | Halpern et al. |
| 3,203,915 A | 8/1965 | D'Aiello |
| 3,221,745 A | 12/1965 | Coover |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender et al. |
| 3,936,486 A | 2/1976 | Egger et al. |
| 3,940,362 A | 2/1976 | Overhults |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flaningam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,523,007 A | 6/1985 | Schipfer et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,743,106 A | 5/1988 | Novicky |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |

(56) References Cited

U.S. PATENT DOCUMENTS

| | | |
|---|---|---|
| 5,064,507 A | 11/1991 | O'Donnell et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,312,864 A | 5/1994 | Wenz et al. |
| 5,328,687 A | 7/1994 | Leung et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 10/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,096,848 A | 8/2000 | Gololobov et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Phrase et al. |
| 6,291,703 B1 | 9/2001 | Schaerfl, Jr. et al. |
| 6,300,045 B2 | 10/2001 | Lobo et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,506,862 B2 | 1/2003 | Cabioch et al. |
| 6,512,023 B1 | 1/2003 | Malofsky et al. |
| 6,518,677 B1 | 2/2003 | Capote et al. |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 * | 6/2004 | Bru-Magniez ...... B01F 17/0028 525/404 |
| 6,794,365 B2 | 9/2004 | Al-Obeidi et al. |
| 6,841,064 B1 | 1/2005 | Weiss et al. |
| 6,846,783 B2 | 1/2005 | Bartley et al. |
| 6,936,140 B2 | 8/2005 | Paxton et al. |
| 7,056,540 B2 | 6/2006 | Yadav et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,465,773 B2 | 12/2008 | Kodemura et al. |
| 7,553,989 B2 | 6/2009 | Sawabe et al. |
| 7,576,234 B2 | 8/2009 | Chorghade et al. |
| 7,603,889 B2 | 10/2009 | Cypes et al. |
| 7,610,775 B2 | 11/2009 | Tonkovich et al. |
| 7,626,477 B2 | 12/2009 | Huang et al. |
| 7,629,416 B2 | 12/2009 | Li et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,829,738 B1 | 11/2010 | Brammer, Jr. et al. |
| 7,900,558 B2 | 3/2011 | Yokoi |
| 8,110,641 B2 | 2/2012 | Lee et al. |
| 8,138,270 B2 | 3/2012 | Sasagawa et al. |
| 8,168,213 B2 | 5/2012 | Kangas et al. |
| 8,247,508 B2 | 8/2012 | Takashima et al. |
| 8,332,437 B2 | 12/2012 | Ballard et al. |
| 8,344,156 B2 | 1/2013 | Umetani et al. |
| 8,425,790 B2 | 4/2013 | Sato et al. |
| 8,425,999 B2 | 4/2013 | McArdle et al. |
| 8,554,938 B2 | 10/2013 | Mittal |
| 8,609,885 B2 | 12/2013 | Malofsky et al. |
| 8,722,831 B2 | 5/2014 | Arai et al. |
| 8,884,051 B2 | 11/2014 | Malofsky et al. |
| 8,975,435 B2 | 3/2015 | Malofsky et al. |
| 8,992,512 B2 | 3/2015 | Richard et al. |
| 8,993,795 B2 | 3/2015 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,220,811 B2 | 12/2015 | Overstreet et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,481,640 B2 | 11/2016 | McArdle et al. |
| 9,505,943 B2 | 11/2016 | Overbeek et al. |
| 9,512,058 B2 | 12/2016 | Malofsky et al. |
| 9,523,008 B2 | 12/2016 | Malofsky et al. |
| 9,752,059 B2 | 9/2017 | Malofsky et al. |
| 10,047,192 B2 | 8/2018 | Ellison et al. |
| 2001/0034300 A1 | 10/2001 | Yurugi et al. |
| 2002/0035231 A1 | 3/2002 | Whitehouse et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0057914 A1 | 3/2004 | Bonda et al. |
| 2004/0076601 A1 | 4/2004 | Bru-Magniez et al. |
| 2005/0056879 A1 * | 3/2005 | Lee et al. ............ C09J 4/00 442/149 |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0120630 A1 | 5/2007 | Huang et al. |
| 2007/0238872 A1 | 10/2007 | Sabesan |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0241485 A1 | 10/2008 | Shimohara et al. |
| 2011/0059104 A1 | 3/2011 | Escandon et al. |
| 2011/0164322 A1 | 7/2011 | Morozumi et al. |
| 2012/0203021 A1 | 8/2012 | Friese et al. |
| 2013/0019520 A1 | 1/2013 | Sello et al. |
| 2013/0281580 A1 | 10/2013 | Malofsky et al. |
| 2013/0303719 A1 | 11/2013 | Malofsky et al. |
| 2013/0324754 A1 | 12/2013 | Bredsguard et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2015/0056879 A1 | 2/2015 | Malofsky et al. |
| 2015/0073110 A1 | 3/2015 | Malofsky et al. |
| 2015/0104660 A1 | 4/2015 | Malofsky et al. |
| 2015/0303122 A1 | 10/2015 | Malofsky et al. |
| 2018/0010014 A1 | 1/2018 | Sweet et al. |

FOREIGN PATENT DOCUMENTS

| | | |
|---|---|---|
| DE | 102017204525 A1 | 9/2017 |
| EP | 2768917 A2 | 8/2014 |
| FR | 2788516 A1 | 7/2000 |
| GB | 432628 A | 7/1935 |
| GB | 965676 A | 8/1964 |
| GB | 965767 A | 8/1964 |
| GB | 975733 A | 11/1964 |

(56) References Cited

FOREIGN PATENT DOCUMENTS

| | | |
|---|---|---|
| GB | 2463065 A | 3/2010 |
| JP | S5681537 A | 7/1981 |
| JP | 63271253 A | 11/1988 |
| JP | H02281013 A | 11/1990 |
| JP | 08231564 H | 9/1996 |
| JP | H08231564 A | 9/1996 |
| JP | 09258448 A | 10/1997 |
| JP | H09258448 A | 10/1997 |
| JP | 2000199936 A | 7/2000 |
| JP | 2002-226316 A | 8/2002 |
| JP | 2003201397 A | 7/2003 |
| JP | 2008174494 A | 7/2008 |
| WO | 1999/046619 A1 | 9/1999 |
| WO | 1999/055394 A1 | 11/1999 |
| WO | 2007/120630 A2 | 10/2007 |
| WO | 2010/091975 A1 | 8/2010 |
| WO | 2010/129068 A1 | 11/2010 |
| WO | 2011043246 A1 | 4/2011 |
| WO | 2011/059104 A1 | 5/2011 |
| WO | 2011/161045 A1 | 12/2011 |
| WO | 2012/054616 A2 | 4/2012 |
| WO | 2012/054633 A2 | 4/2012 |
| WO | 2013059473 A2 | 4/2013 |
| WO | 2013/066629 A1 | 5/2013 |
| WO | 2013/149165 A1 | 10/2013 |
| WO | 2013/149168 A1 | 10/2013 |
| WO | 2013/149173 A1 | 10/2013 |
| WO | 2013149168 A1 | 10/2013 |
| WO | 2017/184986 A1 | 10/2017 |
| WO | 2018/022780 A1 | 2/2018 |
| WO | 2018/022785 A1 | 2/2018 |
| WO | 2018/022788 A1 | 2/2018 |
| WO | 2018/022792 A1 | 2/2018 |
| WO | 2018/022794 A1 | 2/2018 |
| WO | 2018/022804 A1 | 2/2018 |
| WO | 2018/022810 A1 | 2/2018 |
| WO | 2018/053454 A1 | 3/2018 |
| WO | 2018/053503 A1 | 3/2018 |
| WO | 2018/086860 A1 | 5/2018 |

OTHER PUBLICATIONS

Krause et al., J. Polym. Sci.: Part A, 1965, vol. 3, pp. 3573-3586.*
SciFinder Search (Oct. 24, 2020).*
Supplementary European Search Report for co-pending EP Application No. 15 83 9355 dated Feb. 5, 2018.
Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.
M. Ware et al.: "DBU: An Efficient Catalyst for Knoeveganel Condensation under Solvent-free Condition," Bulletin of the Catalysis Society of India, (2007), vol. 6, pp. 104-106.
V. G. Nenajdenko et al.: "Reaction of 2-Methylene-I ,3-Dicarbonyl Compounds Containing a CF3-Group with 1 ,3-Dienes," Tetrahedron, (2000), vol. 56, pp. 6549-6556.
Aldrich's Thermal Transition of Homopolymers.
V. Larras et al., "Synthesis and micellization of amphiphilic poly-(ethylene oxide)-block-poly(methylidene malonate 2.1.2.) diblock copolymers" Macromol. Rapid Commun., vol. 21, Issue 15, (2000), pp. 1089-1092.
M. Fernandez-Garcia et al., "Glass transitions in dimethyl and di-n-butyl poly(itaconate ester)s and their copolymers with methyl methacrylate" Polymer, vol. 38, Issue 6, (1997), pp. 1367-1371.
B. C. Ranu et al., "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," European Journal of Organic Chemistry, Issue 16, (2006), pp. 3767-3770.
H. A. Oskooie et al., "On Water: an Efficient Knoevenagel Condensation using 12-Tungstophosphoric Acid as a Reusable Green Catalyst," Synthetic Communications, vol. 36, issue 19, (2006), pp. 2819-2823.
H. Jiang et al., "Inorganic Zinc Salts Catalyzed Knoevenagel Condensation at Room Temperature without Solvent," Preparative Biochemistry & Biotechnology, (2009), vol. 39, pp. 194-200.
T. Doi et al., "Synthesis of Dimethyl Gloiosiphone a by Way of Palladium-Catalyzed Domino Cyclization," Journal of Organic Chem, vol. 72, Issue 10, (2007), pp. 3667-3671.
H. Jung et al., "New and General Methods for the Synthesis of Arylmethylene Bis(3-Hydroxy-2-Cyclohexene-1-ones) and Xanthenediones by EDDA and In(OTf)3-Catalyzed One-Pot Domino Knoevenagel/Michael or Koevenagel/Michael/Cyclodehydration Reactions," Bull. Korean Chem. Soc. vol. 30, No. 9, (2009), pp. 1989-1995.
P. Klemarczyk, "Adhesion Studies of Mixtures of Ethyl Cyanoacrylate with a Difunctional Cyanoacrylate Monomer and with other Electron-deficient Olefins," J. Adhesion, vol. 69, Issue 3-4, (1999), pp. 293-306.
P. Klemarczyk, "A General Synthesis of 1,1 Disubstituted Electron Deficient Olefins and their Polymer Properties," Polymer, vol. 39, Issue. I, (1998), pp. 173-181.
C. Gill et al., "Knoevenagel condensation in neutral media: A simple and efficient protocol for the synthesis of electrophillic alkenes catalyzed by anhydrous ferric sulphate with remarkable reusability." Bulletin of the Catalysis Society of India 7, (2008), pp. 153-157.
P. Ballesteros et al., "Di-tert-Butyl Methylenemalonate [Propanedioic Acid, Methylene-, bis(1,1-dimethylethyl)ester]," Org. Synth., vol. 64, (1986), pp. 63.
A. M. Vetrova et al., "Improvement of the Thermal Stability of Cyanoacrylate Adhesives," Polymer Science, Series D, vol. 2, No. 1, (2009), pp. 27-30.
A. C. Cope, "Condensation Reactions. I. The Condensation of Ketones with Cyanoacetic Esters and the Mechanism of the Knoevenagel Reaction," Journal of the American Chemical Society, vol. 59, No. 11, (1937), pp. 2327-2330.
G. Lai et al., "Ionic Liquid Functionalized Silica Gel: Novel Catalyst and Fixed Solvent," Tetrahedron Letters, vol. 47, Issue 39, (2006), pp. 6951-6953.
J. R. Harjani et al., "Lewis Acidic Ionic Liquids for the Synthesis of Electrophilic Alkenes via the Knoevenagel Condensation," Tetrahedron Letters, vol. 43, Issue 6, (2002), pp. 1127-1130.
M. Matziari et al., "Active Methylene Phosphinic Peptides: A new Diversification Approach", Organic Letters, vol. 8, No. 11, (2006), pp. 2317-2319.
F. Z. Dorwald, Side Reactions in Organic Synthesis, Preface, Wiley-VCH Verlag GmbH & Co., KgaA, Weinheim, (2005), pp. 1-16.
M. Yamauchi et al., A Facile Conversion of Ethoxydihydropyrans to 4-Cyanoethylisoxazoles, J. Heterocyclic Chem., vol. 33, Issue 2, (1996), pp. 383.
M. Yamauchi et al., "Reactivity of 2-methylene-1,3-dicarbonyl compounds: catalytic enantioselective Diels-Alder reaction", Tetrahedron Asymmetry, vol. 12, Issue 22, (2001), pp. 3113-3118.
C. Schotes et al., "Cu(I)- and C(II)-Catalyzed Cyclo- and Michael Addition Reactions of Unsaturated [beta]-Ketoesters" Journal of Organic Chemistry, vol. 76, No. 14, (2011), pp. 5862-5866.
A. Bugarin et al., "Efficient direct [alpha]-methylenation of carbonyls mediated by diisopropylammonium trifluoroacetate", Chemical Communications, vol. 46, Issue 10, (2010), pp. 1715-1717.
H. Martin et al., "Preparation and Selected Reaction of t-Butyl 2-Methylene-3-oxoalkanoates" Chem. Ber., vol. 124, Issue 11, (1991), pp. 2475-2480.
M. Yamauchi et al., "Reactivity of 2-Methylene-1,3-dicarbonyl Compounds. 1,3-Dipolar Cycloaddition Reaction with Ethyl Diazoacetate", Chem. and Pharm. Bull., vol. 49, No. 12, (2001), pp. 1638-1639.
N. J. Lawrence et al., "Reaction of Baylis-Hillman products with Swern and Dess-Martin oxidants", Tetrahedron Letters, vol. 42, No. 23, (2001), pp. 3939-3941.
J. Vale et al., "Efficient [alpha]-Methylenation of Carbonyl Compounds in Ionic Liquids at Room Temperature", Synlett, vol. 2009, No. 1, (2009), pp. 75-78.
P. Breton et al., "New Poly(Methylidene Malonate 2.1.2) Nanoparticles: Recent Developments", Targeting of Drugs 4, NATO ASI Series, vol. 273, (1994), pp. 161-172.

(56) References Cited

OTHER PUBLICATIONS

C. Limouzin et al., "Anionic Polymerization of n-Butyl Cyanoacrylate in Emulsion and Miniemulsion" Macromolecules, vol. 36, Issue 3, (2003), pp. 667-674.

M. McCoy, "A New Way to Stick" Chemical & Engineering News, vol. 92, Issue 26, (2014), pp. 17-18.

G. B. Bachman et al., "Diethyl Methylenemalonate" Journal of Organic Chemistry, vol. 4, Issue 4, (1939), pp. 493-501.

L. Qifang et al., "Knoevenagel reaction on a molecular sieve", Chinese Science Bulletin, vol. 12, (1961), pp. 914-917.

B. Zuo et al., "Knoevenagel Condensation Over Acidic Zeolite", Chinese Journal of Catalysis, (2002) vol. 23, Issue 6, pp. 557-558.

M. Opanasenko et al., "Comparison of the catalytic activity of MOFs and zeolites in Knoevenagel condensation", Catalysis Science & Technology, vol. 3, (2013), pp. 500-507.

March, Advanced Organic Chemistry, 2d Ed, section 0-25, pp. 365-367, 1977, McGraw Hill, New York, New York.

Morrison and Boyd, Organic Chemistry, 4th Ed., pp. 831 and 836-8, 1983, Allyn Bacon, Inc., Boston, MA.

J. Otera et al., Esterification: Methods, Reactions, and Applications, 2nd Ed., John Wiley & Sons, (2009), pp. 55-58.

A. Hayyan et al., "Esterification of Sludge Palm Oil Using Trifluromethanesulfonic Acid for Preparation of Biodiesel Fuel", Korean Journal of Chemical Engineering, vol. 30, Issue 6, (2013), pp. 1229-1234.

N. Thimmaraju et al., "Transsesterification of diethyl malonate with Benzyl Alcohol Catalyzed by Modified Zirconia: Kinetic Study," Journal of Molecular Catalysis A: Chemical, vol. 391, (2014), pp. 55-65.

G.A. Olah et al., "Superelectrophilic Solvation," Accounts of Chemical Research, vol. 37, No. 4. (2004), pp. 211-220.

A. Kütt et al., "Equilibrium Acidities of Superacids," Journal of Organic Chemistry, vol. 76, No. 2, (2011), pp. 391-395.

N. J. Lee et al., "Syntheses and Toxicity of Monomers and Polymers Containing 5-Fluorouracil" Journal of Macromolecular Science Part A, vol. 29, Issue 2, (1992) pp. 161-172.

N. J. Lee et al., "Synthesis and Toxicity of Monomers and Polymers Containing 5-Fluorouracil" J. Macromol. Sci. Part A, vol. 29, Issue 2, (1992) pp. 161-172.

International Search Report and Written Opinion, Application No. PCT/US15/48846 dated Dec. 4, 2015.

Y. Takagi et al., "Reaction of Active Methylene Radicals with Formaldehyde. I. Synthesis of Diethyl Methylenemalonate" J. Chem. Soc. Japan Ind. Chem. Sect, vol. 56, (1953), pp. 901-903, English abstract.

McNab, Encyclopedia of Chemical Technology, Pyrolysis, Flash Vacuum, 2009, John Wiley & Sons, Inc., pp. 1-26.

P. Block, "Diethyl bis (hydroxymethyl) malonate" Organic Syntheses, vol. 40, (1960), pp. 27-28.

B. M. Reddy et al., "An easy-to-use heterogeneous promoted zirconia catalyst for Knoevenagel condensation in liquid phase under solvent-free conditions." Journal of Molecular Catalysts A: Chemical, vol. 258, (2006), pp. 302-307.

M. Ware et al., "DBU: An Efficient Catalyst for Knoeveganel Condensation under Solvent-free Condition," Bulletin of the Catalysis Society of India, vol. 6, (2007), pp. 104-106.

V. G. Nenajdenko et al., "Reaction of 2-Methylene-1,3-Dicarbonyl Compounds Containing a CF3-Group with 1,3-Dienes," Tetrahedron, vol. 56, Issue 35, (2000), pp. 6549-6556.

J. S. Yadav et al., "Phosphene-Catalyzed Knoevenagel Condensation: a Facile Synthesis of a-Cyanoacrylates and a-Cyanoacrylonitriles," Eur, J, Org, Chem., Issue 3, (2004) pp. 546-551.

Larras et al., Macromol. Rapid Commun. 2000, 21, 1089-1029.

Fernandez-Garcia & Madruga, Polymer 1997, 38(6), 1367-1371.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.

H. Jung et al,: "New and General Methods for the Synthesis of Arylmethylene Bis(3-Hydroxy-2-Cyclohexene-1-Ones) and Xanthenediones by EDDA and in(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,— (1998), vol. 39, No. I, pp. 173-181.

Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.

P, Ballesteros et al.: "D 1-tert-Butyl Methylenemalonate [Propanedioic Acid, Methylene-, bis( 1,1-dimethylethyl)ester]," Organic Syntheses. Coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.

M. Matziari et al. Active Methylene Phosphinic Peptides: A new Diversification Approach Organic Letters 2006 vol. 8, No. 11 pp. 2317-2319 May 5, 2006.

Zaragoza Dorwald, Side Reactions in Organic Synthesis, 2005, Wiley-VCH Verlag GmbH & Co., KgaA, Weinheim, Preface. p. IX.

K. Okamura and T. Date, A Facile Conversion of Ethoxydihydropyrans to 4-Cyanoethylisoxazoles, J. Heterocyclic Chem. 33, 383 (1996).

Yamauchi et al. Tetrahedron Asymetry 12, (2001), 3113-3118.

Cristoph Schotes et al. "Cu(I)- and C(II)-Catalyzed Cyclo- and Michael Addition Reactions of Unsaturated [beta]-Ketoesters" the Journal of Organic Chemistry, vol. 76, No. 14 dated Jul. 15, 2011 p. 5862-5866.

Alejandro Bugarin et al. "Efficient direct [alpha]-methylenation of carbonyls mediated by dissopropylammonium trifluoroacetate", Chemical Communications, vol. 46, No. 10 dated Jan. 25, 2010.

H. Hoffman et al. "Preparation and Selected Reaction of tery-Butyl 2-Methylene-3-oxoalkanoates" Chem. Ber., vol. 124 dated Jan. 1, 1991, pp. 2475-2480.

M. Yamauchi et al. "Reactivity of 2-Methylene-I, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.

Lawrence N J et al. "Reaction of Baylis-Hillman products with Swem and Dess-Martin oxidants", Tetrahedron Letters, Pergamon, GB, vol. 42 No. 23 dated Jun. 4, 2001, pp. 3939-3941.

Juliana Vale et al. "Efficient [alpha]-Methylenation of Carbonyl Compounds in Ionic Liquids at Room Temperature", Synlett, vol. 2009, No. 01, Jan. 1, 2009 (Jan. 1, 2009), pp. 75-78, XP055170349, ISSN: 0936-5214.

DOI: 10.1055/s-0028-1087389 *table 2; compound 3 *.

P. Breton et al., "New Poly(Methylidudene Malonate 2.1.2) Nanoparticles: Recent Developments", Targeting of Drugs 4, NATO ASI Series, vol. 273, pp. I61-172, 1994.

(56) References Cited

OTHER PUBLICATIONS

Limouzin et al., "Anionic Polymerization of n-Butyl Cyanoacrylate in Emulsion and Miniemulsion" Macromolecules, vol. 36, 2003, pp. 667-674.
McCoy, M. "A New Way to Stick" Chemical & Engineering News, vol. 92, Issue 26, Jun. 30, 2014, pp. 17-18, paragraph [2].
Bachman et al., "Diethyl Methylenemalonate" Contirbution from the Research Laboratories of the Eastman Kodak Company, May 17, 1939, pp. 493-501.
"Knoevenagel reaction on a molecular sieve", Li Qifang et al., Chinese Science Bulletin, vol. 12, pp. 914-917. (1988).
"Knoevenagel Condensation Over Acidic Zeolite", Zuo Bojun et al., Chinese Journal ofCatalysis, vol. 23 (6), pp. 555-558. (2002).
"Comparison of the catalytic activity of MOFs and zeolites in Knoevenagel condensation", Maksym Opanasenko, et al., Catalysis Science & Technology, vol. 3 p. 500-507. (2013).
Morrison and Boyd, Organic Chemistry, 4th Ed., pp. 831 and 836-838, 1983, Allyn Bacon, Inc., Boston, MA.
Otera et al., "Esterification: Methods, Reactions, and Applications", 2nct Ed., pp. 55-58, 2010, Wiley-VCH Verlag Gmbh & Co. KGaA. Weinheim, Germany.
"Esterification of Sludge Palm Oil Using Trifluromethanesulfonic Acid for Preparation of Biodiesel Fuel", Korean Journal of Chemical Engineering, Jun. 2013, vol. 30, issue 6, pp. 1229-1234.
Transsesterification of diethyl malonate with Benzyl Alcohol Catalyzed by Modified Zirconia: Kinetic Study, Journal of Molecular Catalysis A: Chemical, vol. 391, Sep. 2014, pp. 55-65.
Olah et al., "Superelectrophilic Salvation," Accounts of Chemical Research, Apr. 2004, vol. 37, No. 4.
Kutt et al., "Equilibrium Acidities of Superacids," Journal of Organic Chemistry, vol. 76, No. 2, 2011, pp. 391-395, published on the web Dec. 17, 2010.
Larras et al. Synthesis and micellization of amphiphilic poly(ethylene oxide)-block-poly(methylidene malonate; 2.1.2.) diblock copolymers Macromol. Rapid Commun. dated2000, vol. 21, pp. 1089-1029.
Yamauchi et al. A Facile Conversion of EthoxydihydroQyrans to 4-. Cvanoethvlisoxazoles, Mar.-Apr. 1996, pp. 383-387.
Lee et al., "Syntheses and Toxicity of Monomers and Polymers Containing 5-Fluorouracil" J. M. S. Pure Appl. Chem. (1992), A29(2), 161-172.
Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
McNab, Kirk-Othmer Encyclopedia of chemical Technology, Pyrolysis, Flash Vacuum, 2009, John Wiley & Sons, Inc., pp. 1-26.
Block, "Diethyl bis (hydroxymethyl) malonate" Organic Syntheses, 1973, Coll. vol. 5, p. 381 [vol. 40, p. 27 (1960); Retrieved on Apr. 4, 2014 from Internet: httg://www.Orgsyn.org/ content/gdfs/ grocedure s/cv5g0381.gdfl.

* cited by examiner

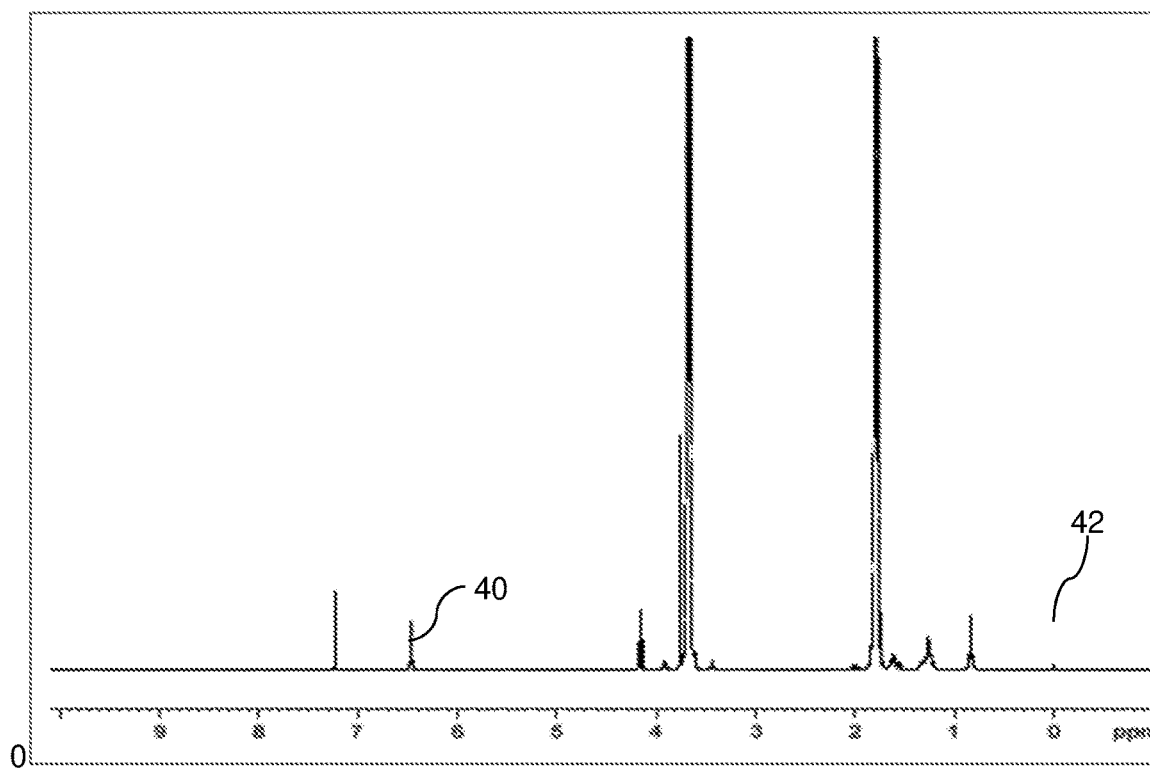
FIG. 1A. NMR spectrogram showing presence of unreacted monomer
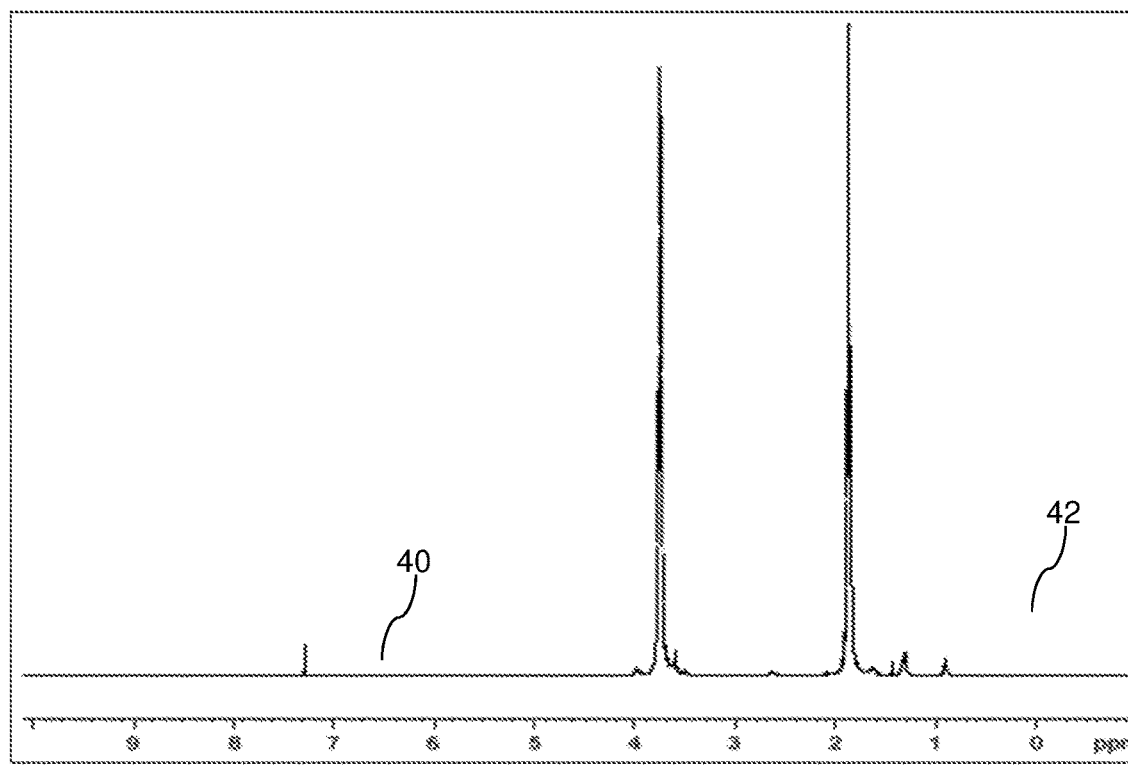
FIG. 1B. NMR spectrogram after polymerization showing ≈100% monomer conversion.

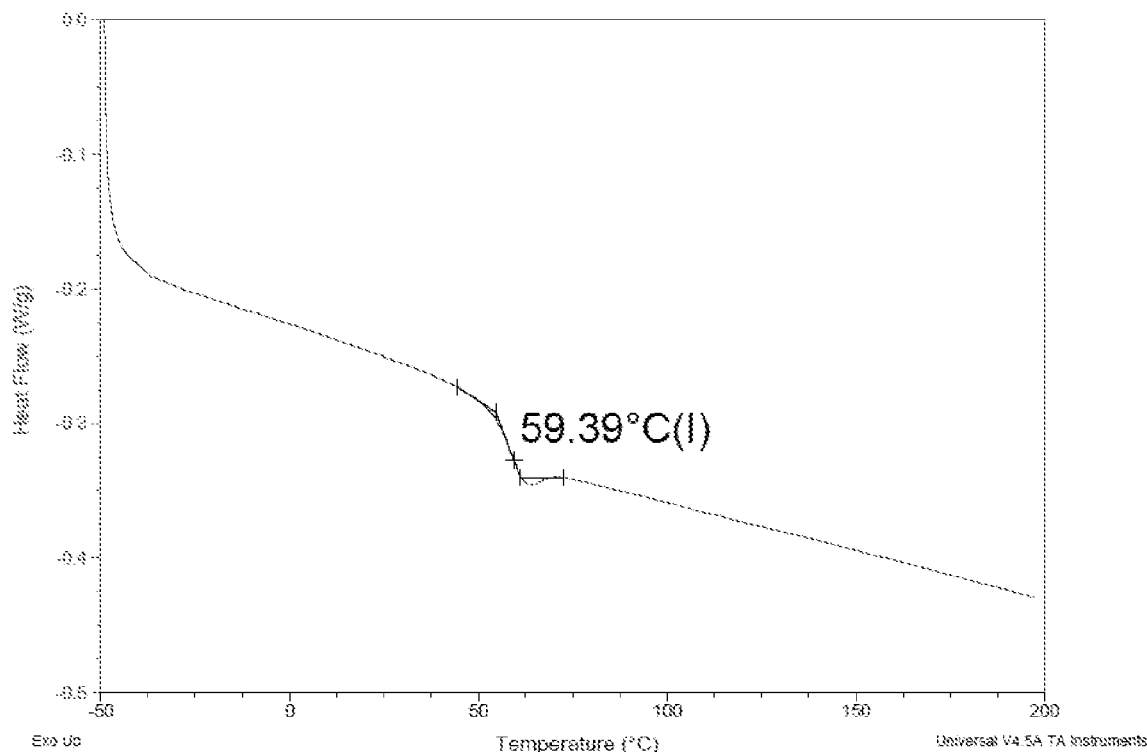
FIG. 2 DSC curve of homopolymer 2-phenyl-1-propanol ethyl methylene malonate.
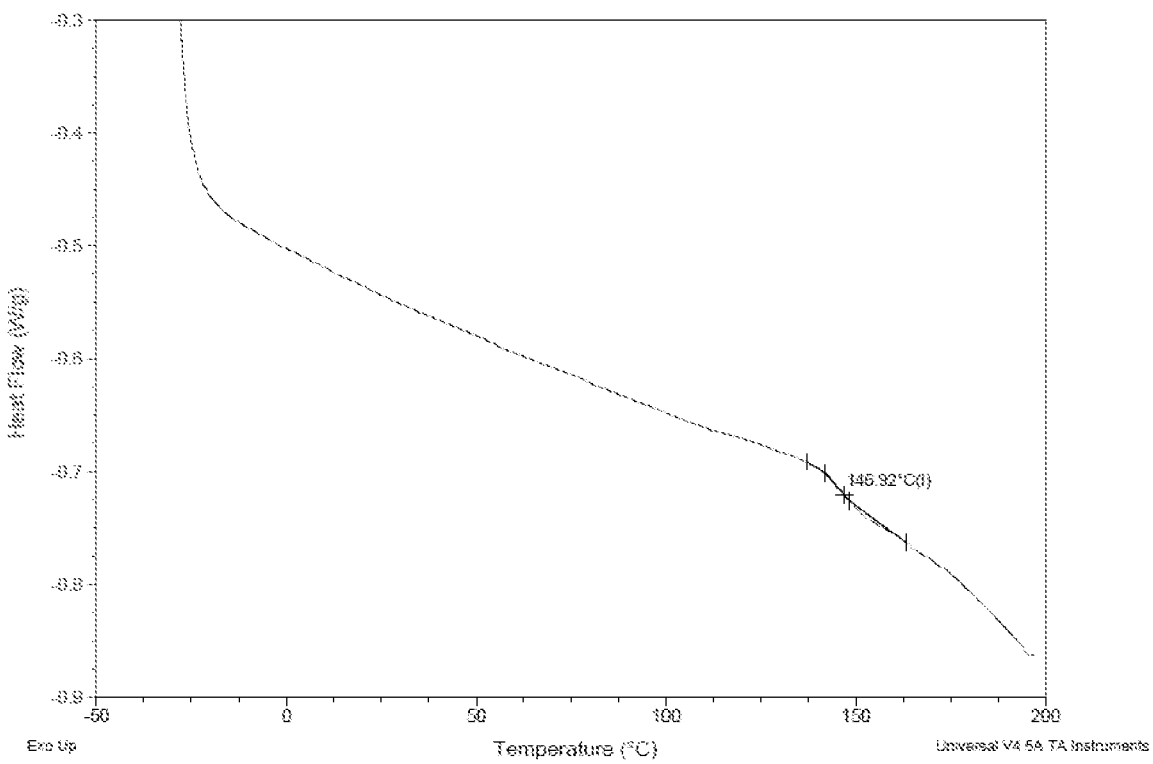
FIG. 3. DSC curve of homopolymer of fenchyl methyl methylene malonate.

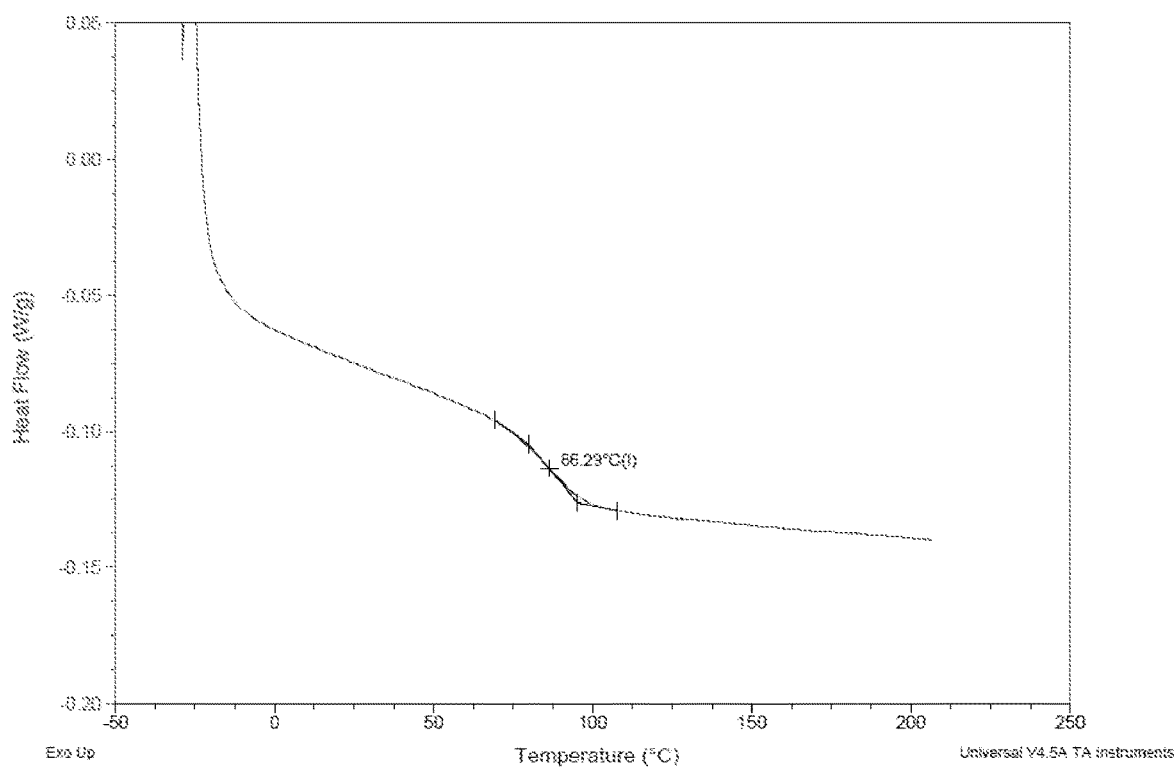
FIG. 4. DSC Curve of homopolymer random copolymer of 2-phenyl-1-propanol ethyl methylene malonate (about 50 weight percent) and fenchyl methyl methylene malonate (about 50 weight percent).

US 11,021,617 B2

POLYMERS INCLUDING ONE OR MORE 1,1-DISUBSTITUTED ALKENE COMPOUNDS AND POLYMER COMPOSITIONS THEREOF

CLAIM OF PRIORITY

The present application is a divisional application of U.S. application Ser. No. 15/509,403 filed on Mar. 7, 2017, which is a United States national filing under 35 U.S.C. 371 of PCT/US2015/048846 filed on Sep. 8, 2015, published as WO 2016/04026. PCT/US2015/048846 claims priority to U.S. patent application Ser. No. 14/789,178 filed on Jul. 1, 2015 published as U.S. Pat. No. 9,249,265, and Ser. No. 14/810,741 filed on Jul. 28, 2015 published as U.S. Pat. No. 9,279,022; and to U.S. Provisional Patent Applications Nos. 62/186,479 filed on Jun. 30, 2015, 62/182,076 filed on Jun. 19, 2015, 62/047,283 filed on Sep. 8, 2014, and 62/047,328 filed on Sep. 8, 2014; all incorporated herein by reference in their entirety.

FIELD

The teachings herein are directed at polymers including one or more 1,1-disubstituted alkene compounds and to compositions including such polymers. The 1,1-disubstituted alkene compound preferably includes two carbonyl groups each bonded to a hydrocarbyl group through a direct bond or through an oxygen atom. The polymer may be a homopolymer or a copolymer.

BACKGROUND

Attempts have been made to employ 1,1-disubstituted alkene alkene compounds in a number of applications such as adhesives, coatings, composites and the like. 1,1-disubstituted alkene compounds are commonly known as methylene malonates. These compounds have been known since the 19$^{th}$ century and in the middle part of the 20$^{th}$ century a number of researchers worked with these compounds, see D'Alelio U.S. Pat. No. 2,330,033; Coover U.S. Pat. No. 3,221,745 and U.S. Pat. No. 3,523,097 Halpern U.S. Pat. No. 3,197,318 and Ponticello U.S. Pat. No. 4,056,543 and U.S. Pat. No. 4,160,864, all incorporated herein by reference in their entirety for all purposes. Despite this work the 1,1-disubstituted alkene alkene compounds have not been commercialized. The disclosed processes for the preparation of these compounds are equilibrium processes which i) also prepare a number of by-products that negatively impact the stability and reactivity of the desired products, ii) which can cause formation of undesired by-products, and iii) which can cause the formation of by-products which prevent reasonable use of the compounds. In addition, some of the by-products and starting materials are difficult to separate from the desired compounds. 1,1-disubstituted alkene alkene compounds polymerize at room temperature under mild conditions which render them both useful and present problems with their stability. The problems with the processes and the products of the processes were not fully appreciated until Malofsky et al. studied the compounds and processes and began developing ways to produce the compounds without the presence of starting materials and by-products that negatively impact their stability and began developing methods of enhancing the stability of such compounds while facilitating cure of the compounds at room temperature and upon demand, see Malofsky et al. U.S. Pat. No. 8,609,885; U.S. Pat. No. 8,884,405; US20140329980; and US20150073110; all incorporated herein by reference in their entirety for all purposes.

The work of Malofsky et al. resulted in commercial interest in 1,1-disubstituted alkene compounds for use in a variety of applications. For many uses the 1,1-disubstituted alkene compounds prepared in the Malofsky et al patents and applications provide advantageous properties and processes.

Many of the 1,1-disubstituted alkene compounds prepared in the Malofsky et al. patents and applications have limited combinations of one or more physical property (e.g., glass transition temperature(s), melting temperature(s) (if any), viscosity, molecular weight, molecular weight distribution) and one or more mechanical property (e.g., tensile properties, elongation at break, impact properties, elastic modulus, shear modulus, adhesion properties, and elastic recovery properties), For a limited number of applications these properties are advantageous. To broaden the application for these compounds it is desirable to develop polymers including one or more 1,1-disubstituted alkene compounds with different molecular architecture and/or different combinations of monomers. Similarly, there is a need for polymers and polymerization processes for achieving a combination of polymerization rates with physical and/or of mechanical properties.

For example, there is a need for polymerization methods, systems, polymerizable compositions, and resulting polymers that allow for improved control of one or more of the following properties of a polymer containing one or more 1,1-disubstituted alkene monomers: the weight average molecular weight, the number average molecular weight, the polydispersity index, the zero-shear viscosity of the polymer (e.g., at one or more temperatures of at least about 20° C. above the melting temperature of the polymer), the viscosity of the polymer system (e.g., the bulk polymer melt or the polymer emulsion) at room temperature, the sequence distribution of monomers in a random copolymer, having at least two different polymer blocks covalently bonded (e.g., each containing one or more 1,1-disubstituted alkene compounds), the glass transition temperature(s) and/or the number of glass transition temperatures, the crystallinity (if any), the melting temperature (if any), the adhesion to substrates (e.g., lap shear strength, breaklose torque), the reaction rate (e.g., the setting time of a composition including the monomers), the tensile properties, the impact properties, or the long chain branching.

SUMMARY

The disclosure relates to polymers including one or more 1,1-disubstituted alkene monomers (i.e., 1,1-disubstituted alkene compounds). The polymer may be prepared using a bulk polymerization process, an emulsion polymerization reaction process (such as an emulsion process including one or more of the features of U.S. patent application Ser. No. 14/789,178 filed on Jul. 1, 2015, see e.g., paragraphs 12 through 18 and 23 through 39, incorporated herein by reference), or a solution process (such as a solution process including one or more of the features of U.S. patent application Ser. No. 14/810,741 filed on Jul. 28, 2015, see e.g. paragraphs 14-22 and 28-95, incorporated herein by reference). The disclosure also relates to articles including these polymers and to the use of the polymers.

Disclosed herein are copolymers including from about 2 weight percent to about 98 weight percent of a first monomer; and from about 2 weight percent to about 98 weight percent of a second monomer; wherein the first monomer is one or more 1,1-disubstituted alkene monomers.

In some embodiments, the first monomer has a structure such that a homopolymer(s) of the first monomer can be polymerized having a Tg of about 25° C. or more (preferably about 35° C. or more, and more preferably about 50° C. or more). For example, the first monomer may include, consist essentially of, or consist entirely of one or monomers selected from the group consisting of diethyl methylene malonate, dimethyl methylene malonate, phenylpropyl ethyl methylene malonate, phenylpropyl methyl methylene malonate, fenchyl methyl methylene malonate, fenchyl ethyl methylene malonate, menthyl ethyl methylene malonate, dicyclohexyl methylene malonate, cyclohexyl ethyl methylene malonate, isobornyl ethyl methylene malonate, benzyl ethyl methylene malonate, benzyl methyl methylene malonate, dibenzyl methylene malonate, and any combination thereof.

In some embodiments, the second monomer has a structure such that homopolymer(s) of the second monomer have a Tg of about 15° C. or less. For example, the second monomer may include, consist essentially of, or consist entirely of one or monomers selected from the group consisting of methylmethoxy ethyl methylene malonate, ethylethoxy ethyl methylene malonate, hexyl methyl methylene malonate, dibutyl methylene malonate, dihexyl methylene malonate, hexyl ethyl methylene malonate, pentyl ethyl methylene malonate, dipentyl methylene malonate, and any combination thereof.

In some embodiments, the copolymer is a block copolymer including a first polymer block attached to a second polymer block, wherein the first polymer block includes the first monomer.

In some embodiments, the block copolymer has (i) a first glass transition temperature (e.g., the first polymer block has first glass transition temperature) of about 25° C. to about 250° C. (e.g., from about 50° C. to about 200° C.). For example, the first polymer block may include about 50 weight percent or more of one or more monomers selected from the group consisting of diethyl methylene malonate, dimethyl methylene malonate, phenylpropyl methyl methylene malonate, fenchyl methyl methylene malonate, fenchyl ethyl methylene malonate, menthyl ethyl methylene malonate, phenyl propyl ethyl methylene malonate, dicyclohexyl methylene malonate, cyclohexyl ethyl methylmalonate, isobornyl ethyl methylene malonate, benzyl ethyl methylene malonate, benzyl methyl methylene malonate, dibenzyl methylene malonate, and any combination thereof.

In some embodiments, the block copolymer has a second glass transition temperature (e.g., the second polymer block has a second glass transition temperature) from about −100° C. to about 15° C. (e.g., from about −80° C. to about 0° C.); or both. For example, the second polymer block may include about 50 weight percent or more of one or more monomers selected from the group consisting of methylmethoxy ethyl methylene malonate, ethylethoxy ethyl methylene malonate, hexyl methyl methylene malonate, dibutyl methylene malonate, dihexyl methylene malonate, hexyl ethyl methylene malonate, pentyl ethyl methylene malonate, dipentyl methylene malonate, and any combination thereof.

In some embodiments, the block copolymer includes three or more polymer blocks.

In some embodiments, the copolymer is a random copolymer. For example, the copolymer may have a blockiness index of about 0.5 or more (e.g., about 0.6 or more, about 0.7 or more, or about 0.8 or more). The blockiness index may be about 1.2 or less (e.g., about 1.1 or less, or about 1.0 or less).

In some embodiments the copolymer (e.g., the block copolymer or the random copolymer) has a single glass transition temperature.

In some embodiments the copolymer has 1 or more long chain branches (e.g., a star polymer having 3 or more arms).

In some embodiments, the copolymer includes one or more multifunctional monomers.

In some embodiments, the copolymer includes a second monomer that is not a 1,1-disubstituted alkene monomer. For example, the second monomer may include, consist essentially of, or consist entirely of one or more acrylates, one or more methacrylates, a styrene, a butadiene, an acrylonitrile, a cyanoacrylate, or any combination thereof.

The disclosure also relates to a polymer including about 50 weight percent or more of a 1,1-disubstituted alkene monomer, wherein the polymer has long chain branch. For example the polymer may be a homopolymer including 98 weight percent or more of the 1,1-disubstituted alkene monomer. As another example, the polymer may be a copolymer including about 2 weight percent or more of a second monomer.

The disclosure also relates to methods of using the polymers, to articles including the polymers, methods of processing the polymers, and to polymeric compositions including the polymers.

BRIEF DESCRIPTION OF THE DRAWINGS

FIGS. 1A and 1B depict representative NMR spectrograms illustrating the conversion of monomer to polymer during polymerization. FIG. 1A is an NMR spectrogram taken at an early stage of the polymerization reaction and the peak at 6.45 ppm, corresponding to the alkene double bond identifies the presence of unreacted monomer. FIG. 1B is taken at the end of the polymerization reaction and there is no detectable peak at 6.45 ppm.

FIGS. 2, 3, and 4 are differential scanning calorimetry (DSC) curves of polymers prepared by anionic polymerization in solution, measured at a heating rate of about 10° C./min using a sample size of about 7 mg showing the glass transition temperature of the polymer. FIG. 2 is a DSC curve of a homopolymer of 2-phenyl-1-propyl ethyl methylene malonate. FIG. 3 is a DSC curve of a homopolymer of fenchyl methyl methylene malonate. FIG. 4 is a DSC curve of a random copolymer of 2-phenyl-1-propyl ethyl methylene malonate (about 50 weight percent) and fenchyl methyl methylene malonate (about 50 weight percent).

FIG. 6 is a representative GPC chromatogram of a homopolymer according to the teachings herein having a low molecular weight and a generally narrow molecular weight distribution.

DETAILED DESCRIPTION

Figure 5A:
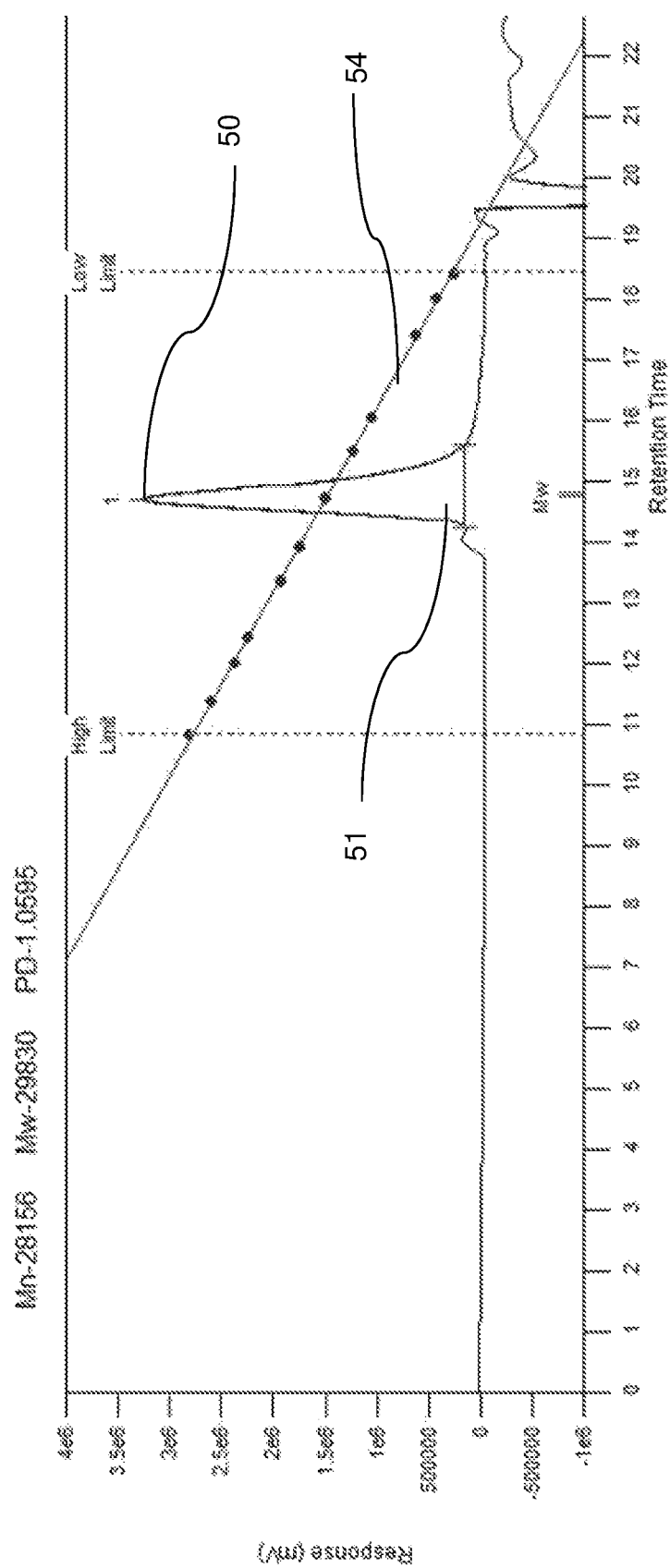
FIGS. 5A, 5B, 5C, and 5D are representative GPC chromatograms of polymers according to the teachings herein. The GPC chromatograms may be employed for the characterization of the number average molecular weight, the number average degree of polymerization, the weight average molecular weight, the weight average degree of polymerization, the polydispersity index, and the molecular weight distribution.

The explanation and illustrations herein are intended to acquaint other skilled in the art with the disclosure, its principles, and its practical application. Accordingly, the specific embodiments of the present invention as set forth are not intended as being exhaustive or limiting of the disclosure. The scope of the disclosure should be determined with reference to the appended claims, along with the full scope of equivalents to which such claims are entitled. The disclosures of all articles and references, including applications and publications, are incorporated by reference for all purposes. Other combinations are also possible as will be gleaned from the following claims, which are also hereby incorporated by reference into this written description.

The disclosure relates to polymers including one or more 1,1-disubstituted alkene monomers. The polymer preferably has combination of monomers and/or a polymer architecture that provides improved properties. For example the polymer may have improvements in one or any combination of the following: physical properties, mechanical properties, adhesion properties and/or reaction rate. In some embodiments the polymer may be a homopolymer. In some embodiments the polymer may be a copolymer. In some embodiments the copolymer may be a random copolymer. In some embodiments the copolymer may be a block copolymer.

The polymer includes, consists essentially of, or consists entirely of one or more 1,1-disubstituted alkene monomers (e.g., one or more 1,1-disubstituted ethylene monomers). 1,1-disubstituted alkene monomers are compounds wherein a central carbon atom is doubly bonded to another carbon atom to form an alkene (e.g.,ethylene) group. The central carbon atom is further bonded to two carbonyl groups. Each carbonyl group is bonded to a hydrocarbyl group through a direct bond or through an oxygen atom, a sulfur atom, or a nitrogen atom. Where the hydrocarbyl group is bonded to the carbonyl group through a direct bond, a keto group is formed. Where the hydrocarbyl group is bonded to the carbonyl group through an oxygen atom, an ester group is formed. The 1,1-disubstituted alkene preferably has a structure as shown below in Formula I, where $X^1$ and $X^2$ are an oxygen atom or a direct bond, and where $R^1$ and $R^2$ are each hydrocarbyl groups that may be the same or different. Both $X^1$ and $X^2$ may be oxygen atoms, such as illustrated in Formula IIA, one of $X^1$ and $X^2$ may be an oxygen atom and the other may be a direct bond, such as shown in Formula IIB, or both $X^1$ and $X^2$ may be direct bonds, such as illustrated in Formula IIC. The 1,1-disubstituted alkene compounds used herein may have all ester groups (such as illustrated in Formula IIA), all keto groups (such as illustrated in Formula IIB) or a mixture thereof (such as illustrated in Formula IIC). Compounds with all ester groups are preferred due to the flexibility of synthesizing a variety of such compounds.

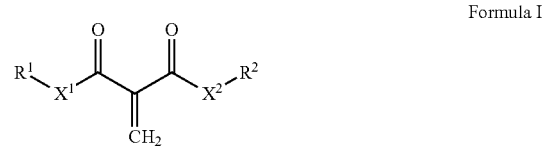

Formula I

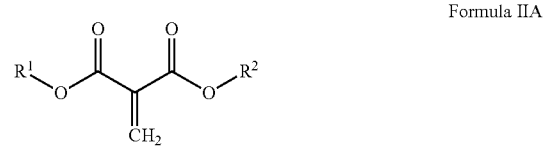

Formula IIA

Formula IIB

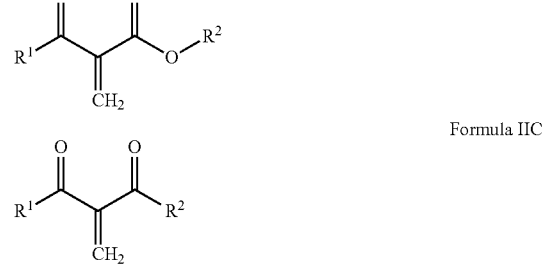

Formula IIC

The oxygen in O—$R^1$ in formula IIA and/or the oxygen atom in O—$R^2$ in formula IIA and formula IIB may be replaced independently by a sulfur atom or a nitrogen atom.

One or more as used herein means that at least one, or more than one, of the recited components may be used as disclosed. Nominal as used with respect to functionality means the theoretical functionality, generally this can be calculated from the stoichiometry of the ingredients used. Generally, the actual functionality is different due to imperfections in raw materials, incomplete conversion of the reactants and formation of by-products. Durability in this context means that the composition once cured remains sufficiently strong to perform its designed function, in the embodiment wherein the cured composition is an adhesive, the adhesive holds substrates together for the life or most of the life of the structure containing the cured composition. As an indicator of this durability, the curable composition (e.g., adhesive) preferably exhibits excellent results during accelerated aging. Residual content of a component refers to the amount of the component present in free form or reacted with another material, such as a polymer. Typically, the residual content of a component can be calculated from the ingredients utilized to prepare the component or composition. Alternatively, it can be determined utilizing known analytical techniques. Heteroatom means nitrogen, oxygen, sulfur and phosphorus, more preferred heteroatoms include nitrogen and oxygen. Hydrocarbyl as used herein refers to a group containing one or more carbon atom backbones and hydrogen atoms, which may optionally contain one or more heteroatoms. Where the hydrocarbyl group contains heteroatoms, the heteroatoms may form one or more functional groups well known to one skilled in the art. Hydrocarbyl groups may contain cycloaliphatic, aliphatic, aromatic or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. One or both hydrocarbyl groups may consist of one or more carbon atoms and one or more hydrogen atoms. As used herein percent by weight or parts by weight refer to, or are based on, the weight of the emulsion composition unless otherwise specified.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

1,1-disubstituted alkene compound means a compound having a carbon with a double bond attached thereto and which is further bonded to two carbon atoms of carbonyl groups. A preferred class of 1,1-disubstituted alkene compounds are the methylene malonates which refer to compounds having the core formula

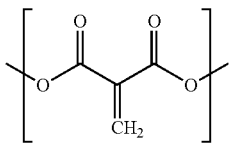

The term "monofunctional" refers to 1,1-disubstituted alkene compounds or a methylene malonates having only one core formula. The term "difunctional" refers to 1,1-disubstituted alkene compounds or a methylene malonates having two core formulas bound through a hydrocarbyl linkage between one oxygen atom on each of two core formulas. The term "multifunctional" refers to 1,1-disubstituted alkene compounds or methylene malonates having more than one core formula which forms a chain through a hydrocarbyl linkage between one oxygen atom on each of two adjacent core formulas. The term "latent acid-forming impurities" or "latent acid-forming impurity" refers to any impurity that, if present along with the 1,1-disubstituted alkene compounds or methylene malonates, will with time be converted to an acid. The acid formed from these impurities may result in overstabilization of the 1,1-disubstituted alkene compounds, thereby reducing the overall quality and reactivity of the compounds. The term "keto" refers to a molecule having a ketal functionality; i.e., a molecule containing a carbon bonded to two —OR groups, where O is oxygen and R represents any alkyl group. The terms "volatile" and "non-volatile" refers to a compound which is capable of evaporating readily at normal temperatures and pressures, in the case of volatile; or which is not capable of evaporating readily at normal temperatures and pressures, in the case of non-volatile. As used herein, the term "stabilized" (e.g., in the context of "stabilized" 1,1-disubstituted alkene compounds or monomer compositions comprising same) refers to the tendency of the compounds (or the monomer compositions), prior to activation with an activator, to substantially not polymerize with time, to substantially not harden, form a gel, thicken, or otherwise increase in viscosity with time, and/or to substantially show minimal loss in cure speed (i.e., cure speed is maintained) with time. As used herein, the term "shelf-life" (e.g., as in the context of 1,1-disubstituted alkene compounds having an improved "shelf-life") refers to the 1,1-disubstituted alkene compounds which are stabilized for a given period of time; e.g., 1 month, 6 months, or even 1 year or more. As used herein, bulk polymerization refers to the polymerization of a polymerizable composition including one or more monomers where the concentration of the one or more monomers is about 80 weight percent or more, preferably about 90 weight percent or more (e.g., about 100 weight percent), based on the total weight of the compounds in the polymerizable composition that are liquid at room temperature. As used herein, a copolymer having a generally blocky sequence distribution of monomers may be characterized as having a blockiness index of about 0.7 or less, about 0.6 or less, about 0.5 or less, about 0.4 or less, or about 0.3 or less.

The hydrocarbyl groups (e.g., $R^1$ and $R^2$), each comprise straight or branched chain alkyl, straight or branched chain alkenyl, straight or branched chain alkynyl, cycloalkyl, alkyl substituted cycloalkyl, aryl, aralkyl, or alkaryl. The hydrocarbyl group may optionally include one or more heteroatoms in the backbone of the hydrocarbyl group. The hydrocarbyl group may be substituted with a substituent that does not negatively impact the ultimate function of the monomer or the polymer prepared from the monomer. Preferred substituents include alkyl, halo, alkoxy, alkylthio, hydroxyl, nitro, cyano, azido, carboxy, acyloxy, and sulfonyl groups. More preferred substituents include alkyl, halo, alkoxy, alylthio, and hydroxyl groups. Most preferred substituents include halo, alkyl, and alkoxy groups.

As used herein, alkaryl means an alkyl group with an aryl group bonded thereto. As used herein, aralkyl means an aryl group with an alkyl group bonded thereto and include alkylene bridged aryl groups such as diphenyl methyl groups or diphenyl propyl groups. As used herein, an aryl group may include one or more aromatic rings. Cycloalkyl groups include groups containing one or more rings, optionally including bridged rings. As used herein, alkyl substituted cycloalkyl means a cycloalkyl group having one or more alkyl groups bonded to the cycloalkyl ring.

Preferred hydrocarbyl groups include 1 to 30 carbon atoms, more preferably 1 to 20 carbon atoms, and most preferably 1 to 12 carbon atoms. Preferred hydrocarbyl groups with heteroatoms in the backbone are alkyl ethers having one or more alkyl ether groups or one or more alkylene oxy groups. Preferred alkyl ether groups are ethoxy, propoxy, and butoxy.

One or more of the hydrocarbyl groups (e.g., $R^1$, $R^2$, or both), preferably includes a $C_{1-15}$ straight or branched chain alkyl, a $C_{1-15}$ straight or branched chain alkenyl, a $C_{5-18}$ cycloalkyl, a $C_{6-24}$ alkyl substituted cycloalkyl, a $C_{4-18}$ aryl, a $C_{4-20}$ aralkyl, or a $C_{4-20}$ alkaryl. More preferably, the hydrocarbyl group, includes a $C_{1-8}$ straight or branched chain alkyl, a $C_{5-12}$ cycloalkyl, a $C_{6-12}$ alkyl substituted cycloalkyl, a $C_{4-18}$ aryl, a $C_{4-20}$ aralkyl, or a $C_{4-20}$ alkaryl.

Preferred alkyl groups include methyl, propyl, isopropyl, butyl, tertiary butyl, hexyl, ethyl pentyl, heptyl and octyl groups. More preferred alkyl groups include methyl and ethyl. Preferred cycloalkyl groups include cyclohexyl and fenchyl. Preferred alkyl substituted groups include menthyl and isobornyl.

Most preferred hydrocarbyl groups attached to the carbonyl group include methyl, ethyl, propyl, isopropyl, butyl, tertiary, pentyl, hexyl, heptyl, octyl, fenchyl, menthyl, and isobornyl.

The 1,1-disubstituted alkene monomer (e.g., the 1,1-disubstituted ethylene monomer) may be a symmetric monomer including two carbonyls (e.g. bonded ethylene to the ethylene)and having hydrocarbyl groups that are the same and are both directly connected or are both connected by an oxygen atom to the two carbonyls.

The 1,1-disubstituted alkene monomer (e.g., the 1,1-disubstituted ethylene monomer) may be an assymmetric monomer including two carbonyls (e.g. bonded ethylene to the ethylene)and having hydrocarbyl groups that are different and/or that are bonded differently to the two carbonyls (e.g., one bonded directly and one bonded by an oxygen atom).

Particularly preferred monomers include methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-N-propyl methylene malonate, ethyl hexyl methylene malonate, methyl fenchyl methylene malonate, ethyl fenchyl methylene malonate, 2 phenylpropyl ethyl methylene malonate, 3 phenylpropyl ethyl methylene malonate, and dimethoxy ethyl methylene malonate.

Some or all of the 1,1-disubstituted alkenes can also be multifunctional having more than one core unit and thus more than one alkene group. Exemplary multifunctional 1,1-disubstituted alkenes are illustrated by the formula:

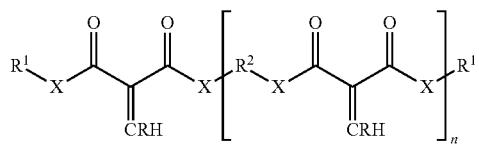

wherein $R^1$, $R^2$ and X are as previously defined; n is an integer of 1 or greater; and R is a hydrocarbyl group, and the 1,1-disubstituted alkene has n+1 alkenes. Preferably n is 1 to about 7, and more preferably 1 to about 3, and even more preferably 1. In exemplary embodiments $R^2$ is, separately in each occurrence, straight or branched chain alkyl, straight or branched chain alkenyl, straight or branched chain alkynyl, cycloalkyl, alkyl substituted cycloalkyl, aryl, aralkyl, or alkaryl, wherein the hydrocarbyl groups may contain one or more heteroatoms in the backbone of the hydrocarbyl group and may be substituted with a substituent that does not negatively impact the ultimate function of the compounds or polymers prepared from the compounds. Exemplary substituents are those disclosed as useful with respect to $R^1$. In certain embodiments $R^2$ is, separately in each occurrence, $C_{1-15}$ straight or branched chain alkyl, $C_{2-15}$ straight or branched chain alkenyl, $C_{5-18}$ cycloalkyl, $C_{6-24}$ alkyl substituted cycloalkyl, $C_{4-18}$ aryl, $C_{4-20}$ aralkyl or $C_{4-20}$ alkaryl groups. In certain embodiments $R^2$ is separately in each occurrence $C_{1-8}$ straight or branched chain alkyl, $C_{5-12}$ cycloalkyl, $C_{6-12}$ alkyl substituted cycloalkyl, $C_{4-18}$ aryl, $C_{4-20}$ aralkyl or $C_{4-20}$ alkaryl groups.

It will be appreciated according to the teaching herein, the one or more monomer may include a comonomer that is a 1,1-disubstituted alkene compound having a hydrocarbyl group bonded to each of the carbonyl groups through a direct bond (e.g., a carbon-carbon bond) or an oxygen atom, such as a monomer having one or more features described above. If included, a comonomer may optionally be a monomer that is not a 1,1-disubstituted alkene compound. Any comonomer capable of anionic or free radical polymerization may be employed. For example, the comonomer may be capable of forming a random copolymer with a 1,1-disubstituted alkene compound, capable of forming a block copolymer with a 1,1-disubstituted alkene compound, or both.

The 1,1-disubstituted alkene monomer preferably is prepared using a method which results in a sufficiently high purity so that it can be polymerized. The purity of the 1,1-disubstituted alkene compound may be sufficiently high so that 70 mole percent or more, preferably 80 mole percent or more, more preferably 90 mole percent or more, even more preferably 95 mole percent or more, and most preferably 99 mole percent or more of the 1,1-disubstituted alkene compound is converted to polymer during a polymerization process. The purity of the 1,1-disubstituted alkene compound preferably is about 85 mole percent or more, more preferably about 90 mole percent or more, even more preferably about 93 mole percent or more, even more preferably about 95 mole percent or more, even more preferably about 97 mole percent or more, and most preferably about 97 mole percent or more, based on the total moles of the 1,1-disubstituted alkene compound. If the 1,1-disubstituted alkene compound includes impurities, preferably about 40 mole percent or more, more preferably about 50 mole percent or more of the impurity molecules are the analogous 1,1-disubstited alkane compound. The concentration of any impurities having a dioxane group preferably is about 2 mole percent or less, more preferably about 1 mole percent or less, even more preferably about 0.2 mole percent or less, and most preferably about 0.05 mole percent or less, based on the total moles of the 1,1-disubstituted alkene compound. The total concentration of any impurity having the alkene group replaced by an analogous hydroxyalkyl group (e.g., by a Michael addition of the alkene with water), preferably is about 3 mole percent or less, more preferably about 1 mole percent or less, even more preferably about 0.1 mole percent or less, and most preferably about 0.01 mole percent or less, based on the total moles in the 1,1-disubstituted alkene compound. Preferred 1,1-disubstituted alkene compounds are prepared by a process including one or more (e.g., two or more) steps of distilling a reaction product or an intermediate reaction product (e.g., a reaction product or intermediate reaction product of a source of formaldehyde and a malonic acid ester).

The polymer may be a homopolymer or a copolymer, such as a random copolymer or a block copolymer. The homopolymer or copolymer includes one or more 1,1-disubstituted alkene monomers according to the teachings herein. Preferably, the total amount of the 1,1-disubstituted alkene monomer in the polymer (or in a polymer block of a block copolymer) is about 2 weight percent or more, more preferably about 5 weight percent even more preferably about 30 weight percent or more, even more preferably about 50 weight percent or more, and even more preferably about 70 weight percent or more, based on the total weight of the polymer. For example, the polymer may consist essentially of, or entirely of 1,1-disubstituted alkene monomers. As another example, the polymer may be a block copolymer having one or more of the polymer blocks that individually consist essentially of, or entirely of the 1,1-disubstituted alkene containing compounds.

The polymer may be a block copolymer. A block copolymer may be prepared by any method that results in two or more different blocks on the same polymer chain. For example a block copolymer may be prepared by combining different polymer chains (e.g., as an end graft, as a side graft, or both) or using a process including multi-stage addition of different monomers during the polymerization to achieve a block copolymer having polymer blocks with different compositions. For example, a block copolymer may have a first polymer block, (block A), and a second polymer block (block B). The block copolymer may have 2 or more blocks or 3 or more blocks. The A block and B block may include at least one monomer that is the same (however at different concentrations), or may include only monomers that are different. For example, the A block may be a homopolymer of a first monomer, and the B block may include one or more second monomers which are each different from the first monomer. The first polymer block may be a homopolymer or a copolymer (e.g., a random copolymer). The second polymer block may be a homopolymer or a copolymer (e.g., a random copolymer). The first polymer block and the second polymer block preferably each include one or more 1,1-disubstituted alkene monomer according to the teachings herein. Preferably, the amount of the 1,1-disubstituted alkene monomer in the first polymer block and/or in the second polymer block is about 30 weight percent or more, preferably about 50 weight percent or more, even more preferably about 70 weight percent or more, based on the total weight of the polymer block. For example, one or more of the polymer blocks may consist essentially of, or entirely of 1,1-disubstituted alkene monomer(s). It will be appreciated that one or more blocks may be substantially or entirely free of any 1,1-disubstituted alkene containing compounds. For example, one or more of the polymer blocks may include one or more conjugated diene monomers and/or one or more styrenic monomers.

The polymers preferably are prepared using monomer and/or methods that result in a high conversion of the monomer to polymer. The conversion of monomer to polymer may be measured using NMR spectroscopy, such as illustrated in FIG. 1A and FIG. 1B, corresponding to an early and a later stage of a propagation reaction for polymerizing a 1,1-disubstituted alkene monomer. Here, the monomer is diethyl methylene malonate and the concentration of the monomer can be monitored by the peak at about 6.45 ppm 40 corresponding to the reactive double bond of the monomer. Hexamethyldisiloxane is used here an internal standard (i.e., internal reference) 42 and is seen at about 0 ppm. It will be appreciated that other compounds may be employed as an internal standard. In FIG. 1A, the NMR spectrogram was measured on a first aliquot taken from a specimen initiated with sodium benzoate at a molar ratio of monomer to initiator of about 100:1. The first aliquot was taken after the reaction had propagated for about 30 seconds at room temperature. The first aliquot was quenched with an acid to stop the propagation reaction. FIG. 1B shows the NMR spectrogram from a second aliquot taken from the same specimen after about 5 minutes of the propagation reaction. As seen in FIG. 1B, the monomer is no longer detectable as evidenced by a lack of the reactive double bond peak at about 6.45 ppm 40.

The polymers according to the teachings herein preferably have a number average molecular weight or a weight average molecular weight that is about 700 g/mole or more, more preferably about 2,000 g/mole or more, even more preferably about 10,000 g/mole or more, and most preferably about 20,000 g/mole or more. The molecular weight of the polymer may be sufficiently low so that the polymer may be easily processed. The number average molecular weight or the weight average molecular weight preferably is about 3,000,000 g/mole or less, more preferably about 1,000,000 g/mole or less, even more preferably about 500,000 g/mole or less, and most preferably about 200,000 g/mole or less.

The polymer may be a relatively low molecular weight polymer having a number average molecular weight of about 40,000 g/mole or less, about 30,000 g/mole or less, or about 20,000 g/mole or less. The polymer may be a relatively high molecular weight polymer having a number average molecular weight of greater than 40,000 g/mole, about 60,000 g/mole or more, or about 100,000 g/mole or more.

The polymer may be characterized by a polydispersity index of about 1.00 or more or about 1.05 or more. The polymer may be characterized by a polydispersity index of about 10 or less, preferably about 7 or less, more preferably about 4 or less, and most preferably about 3 or less. In some embodiments, the polymer may have a narrow molecular weight distribution such that the polydispersity index is about 2.3 or less, about 1.9 or less, about 1.7 or less, about 1.5 or less, or about 1.3 or less.

Figure 5B:
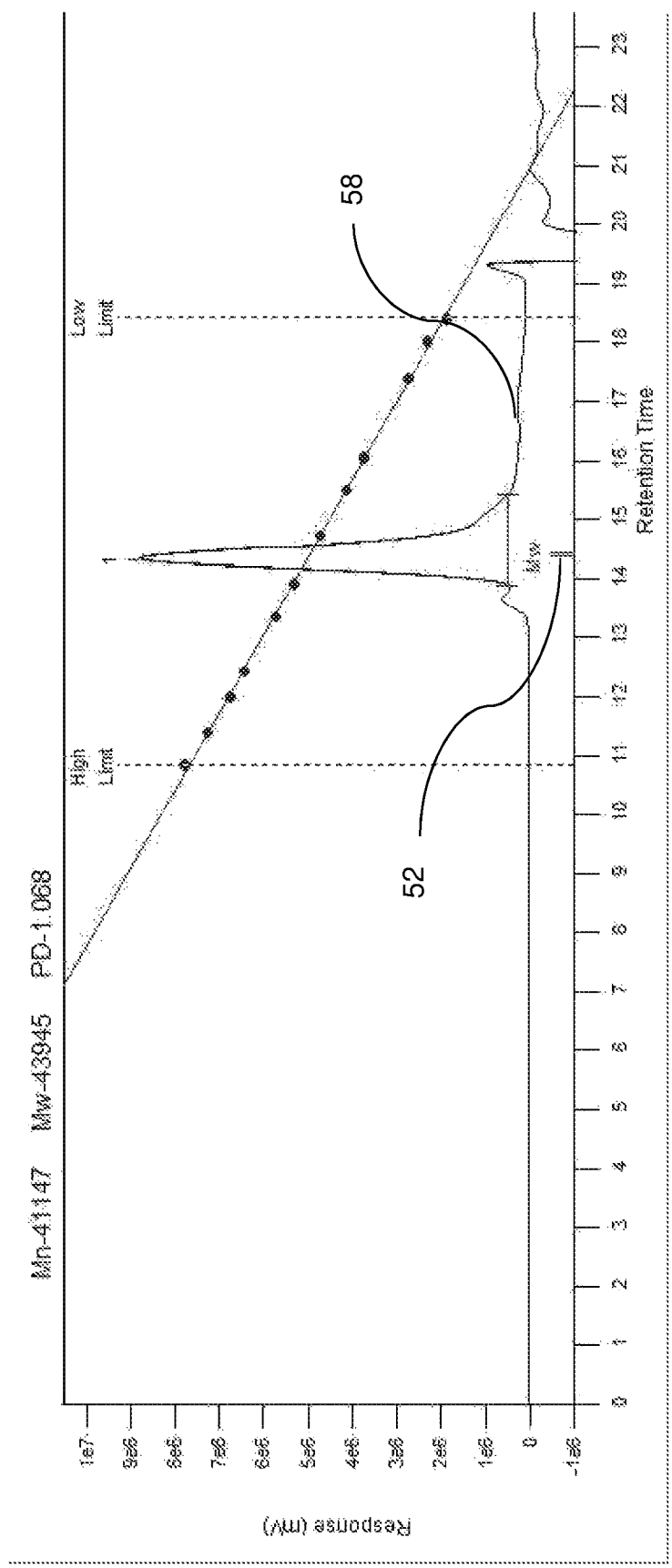
Figure 5C:
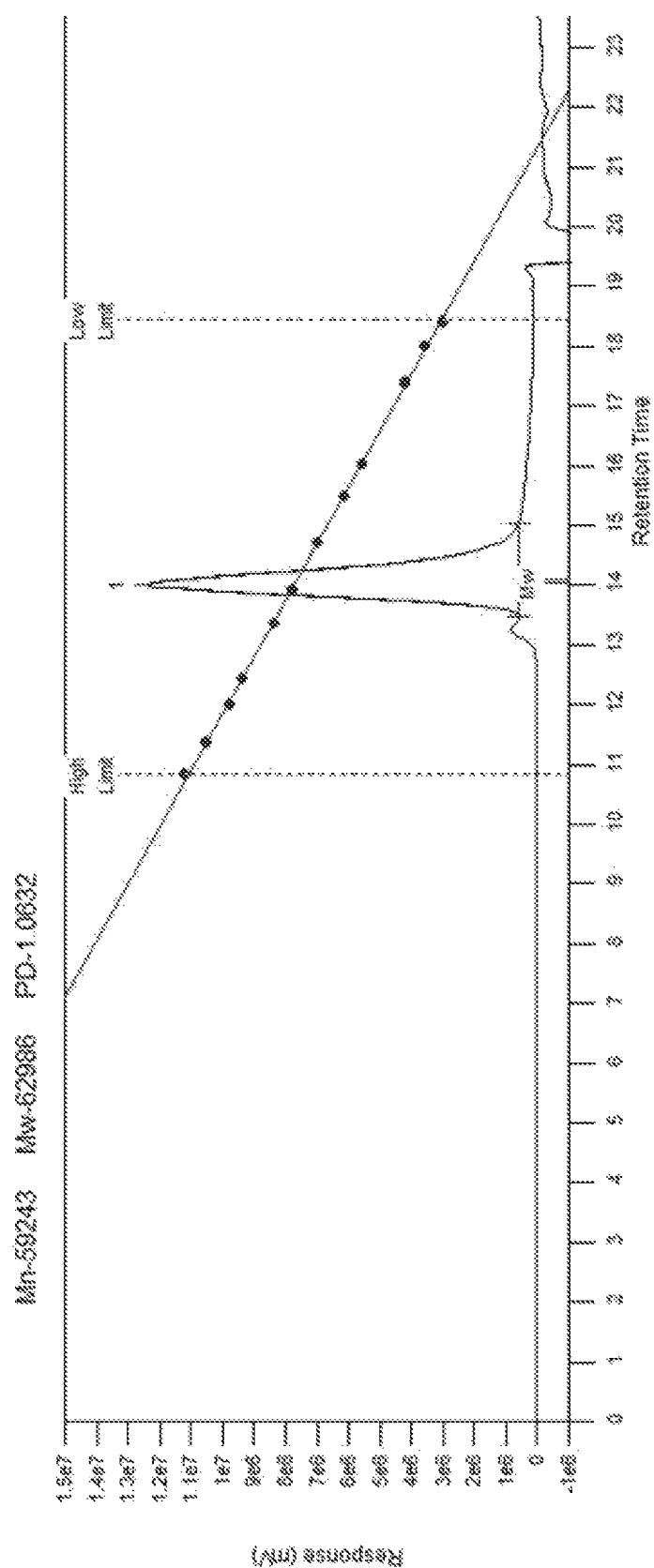
Figure 5D:
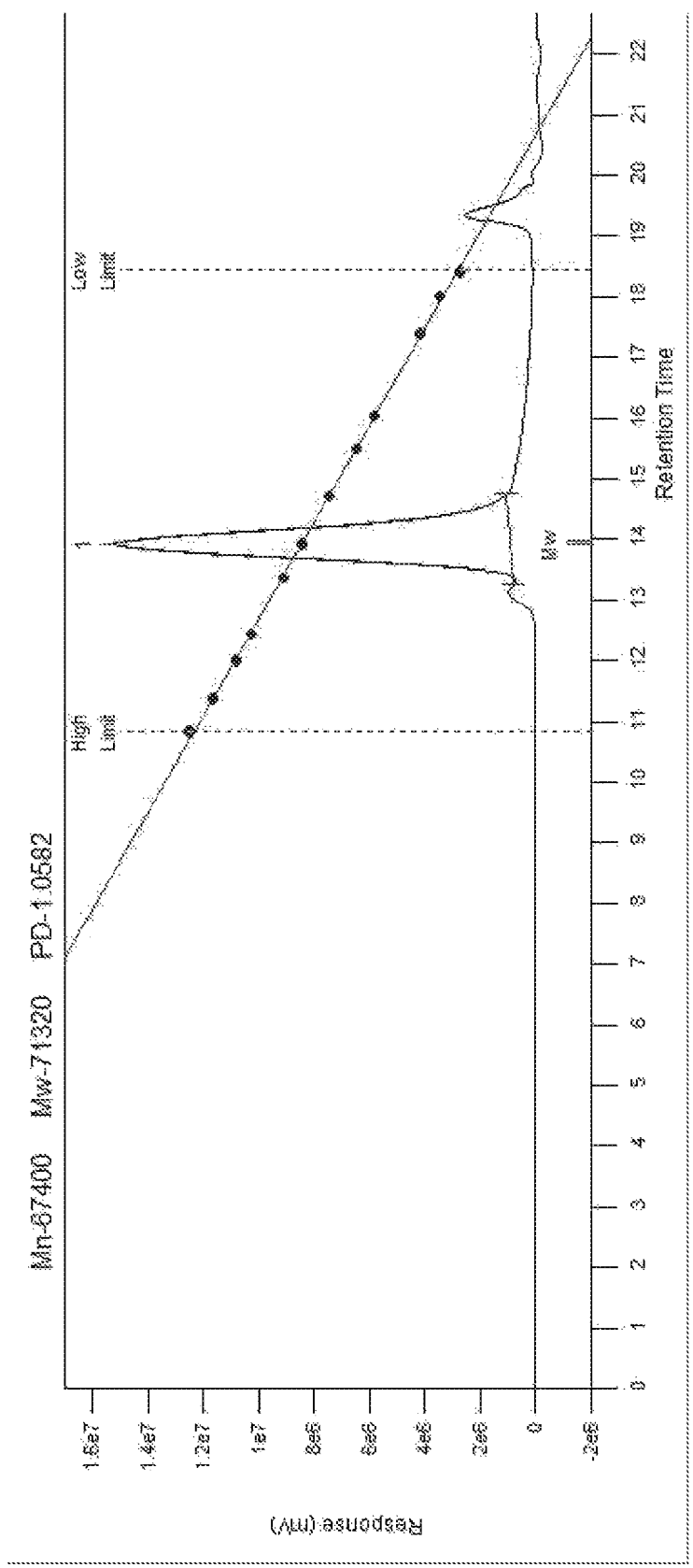
Figure 6:
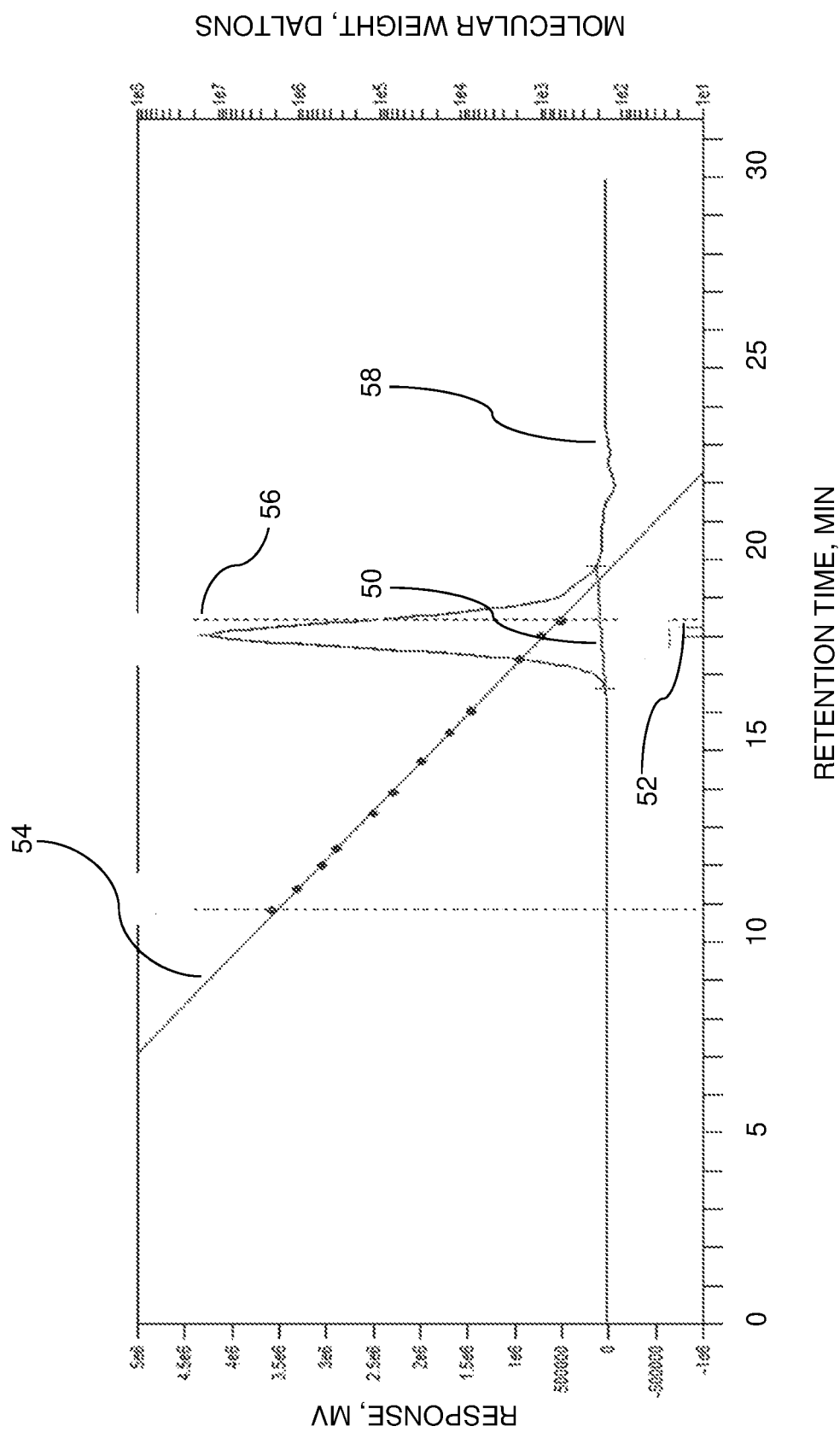
FIG. 6 is a representative GPC chromatogram of a polymer according to the teachings herein.
Figure 7:
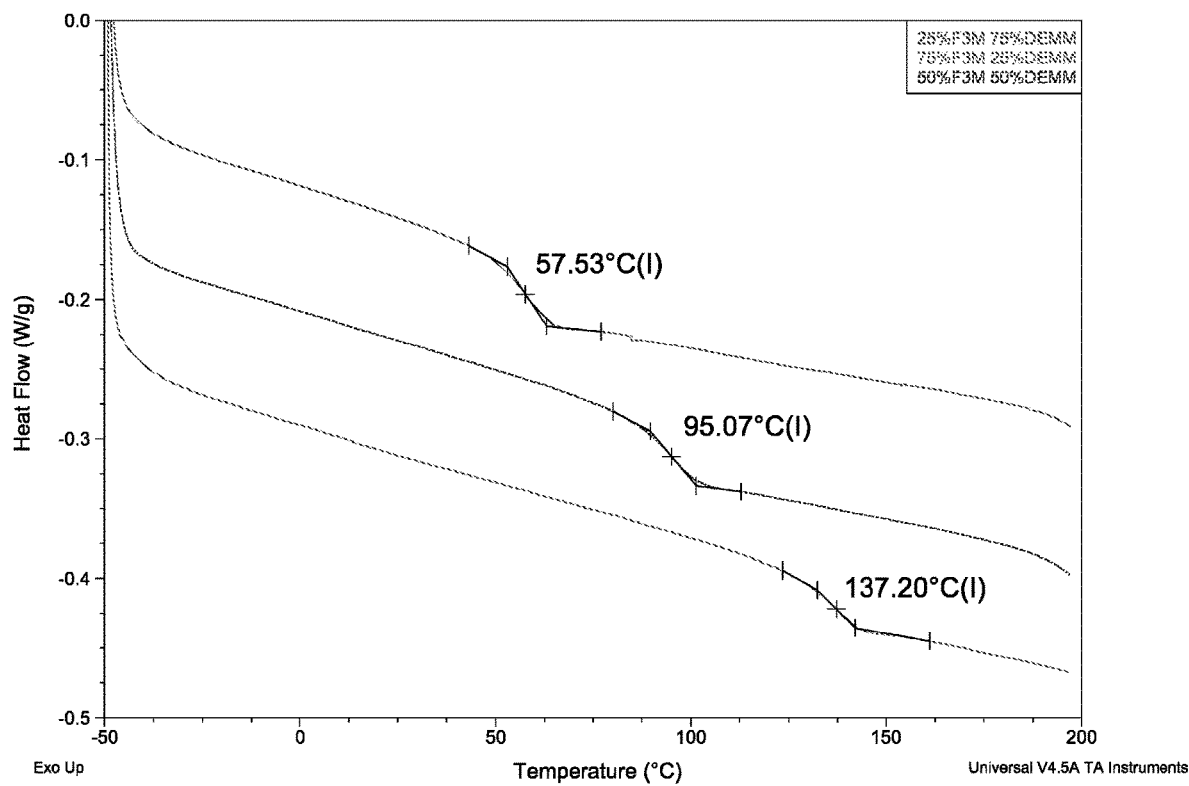
FIG. 7 shows 3 illustrative differential scanning calorimetry curves (DSC) of random copolymers of fenchyl methyl methylene malonate and diethyl methylene malonate with weight ratio of monomer of 75:25, 50:50, and 25:75. Each random copolymer has a single glass transition temperature. DSC trace of the random copolymers of DEMM and F3M in various ratios. At about 25 weight percent F3M, the glass transition temperature is about 57.5° C. At about 50 weight percent F3M, the glass transition temperature is about 95.1° C. At about 75 weight percent F3M, the glass transition temperature is about 137.2° C. Each of these random copolymers has a single glass transition temperature.
Figure 8A:
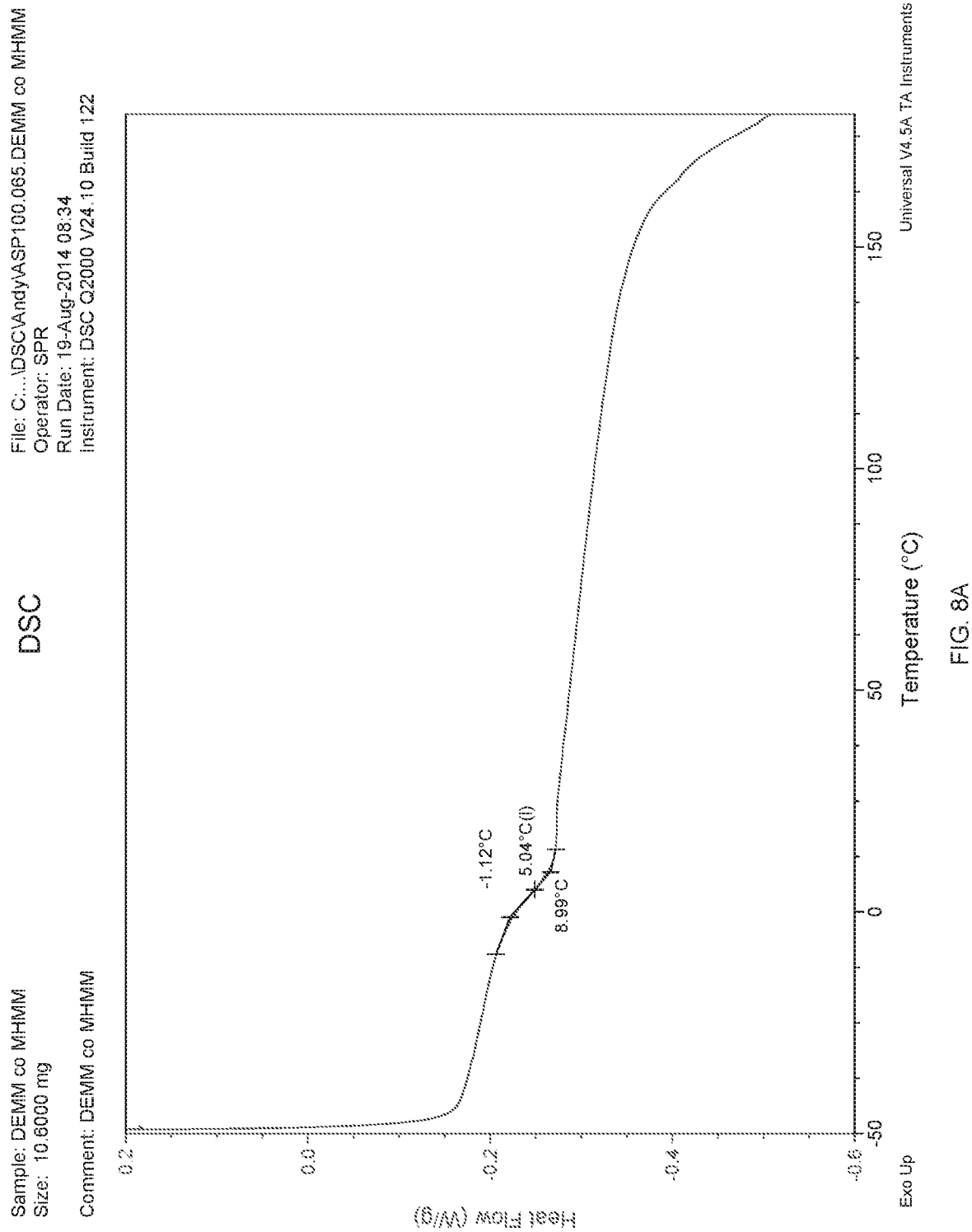
FIG. 8A and FIG. 8B are DSC curves of random copolymers made of 50 weight percent DEMM and 50 weight percent MHMM prepared in solution of hexane and DCM respectively. Although each random copolymer has a single glass transition temperature, the glass transition temperature may be affected by the solvent. The DSC curves do not show a melting peak indicating the breakdown of crystallinity of DEMM achieved with the addition of MHMM. It also represents the absence of a block of poly(DEMM).
Figure 8B:
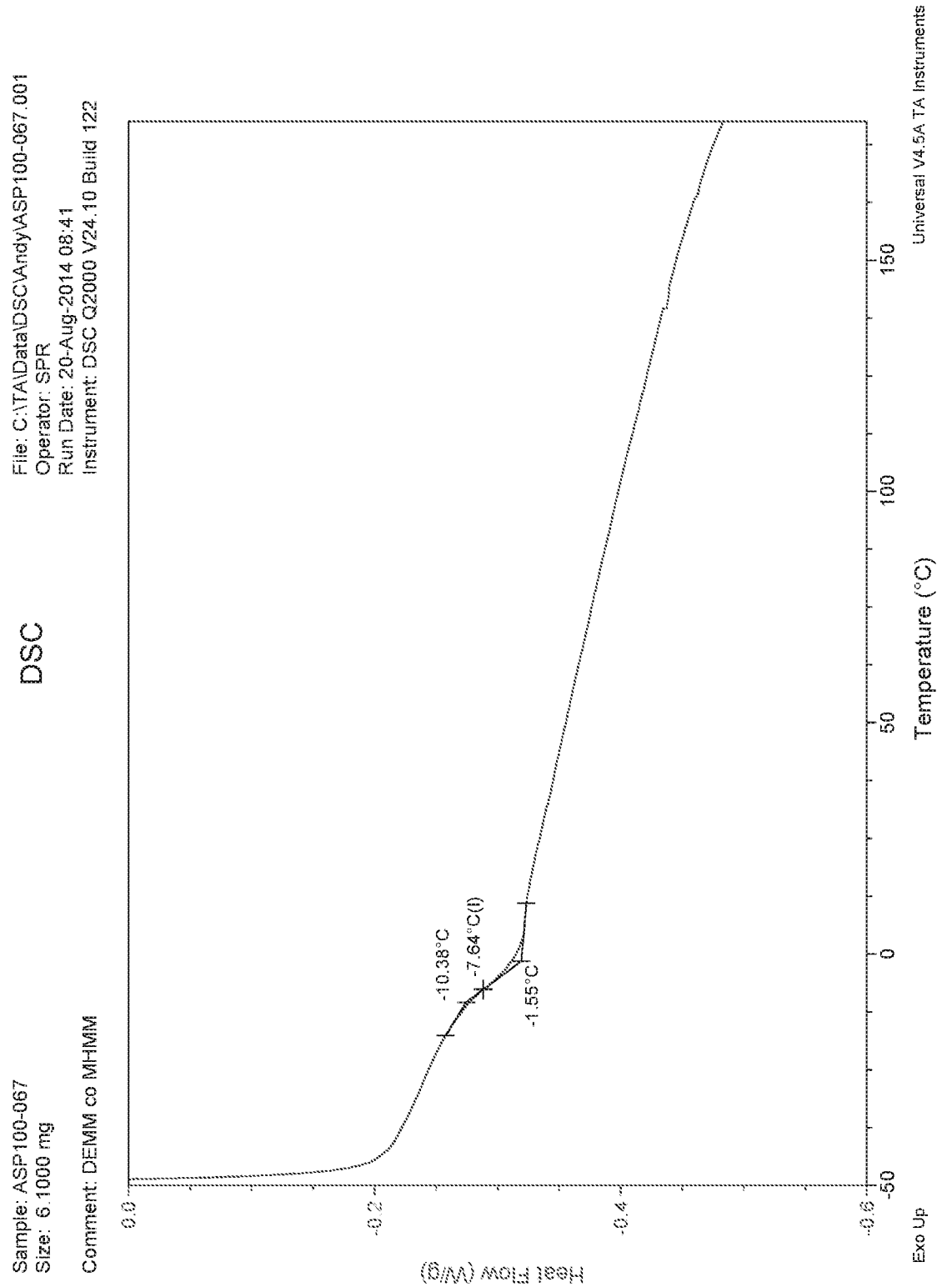
Figure 8C:
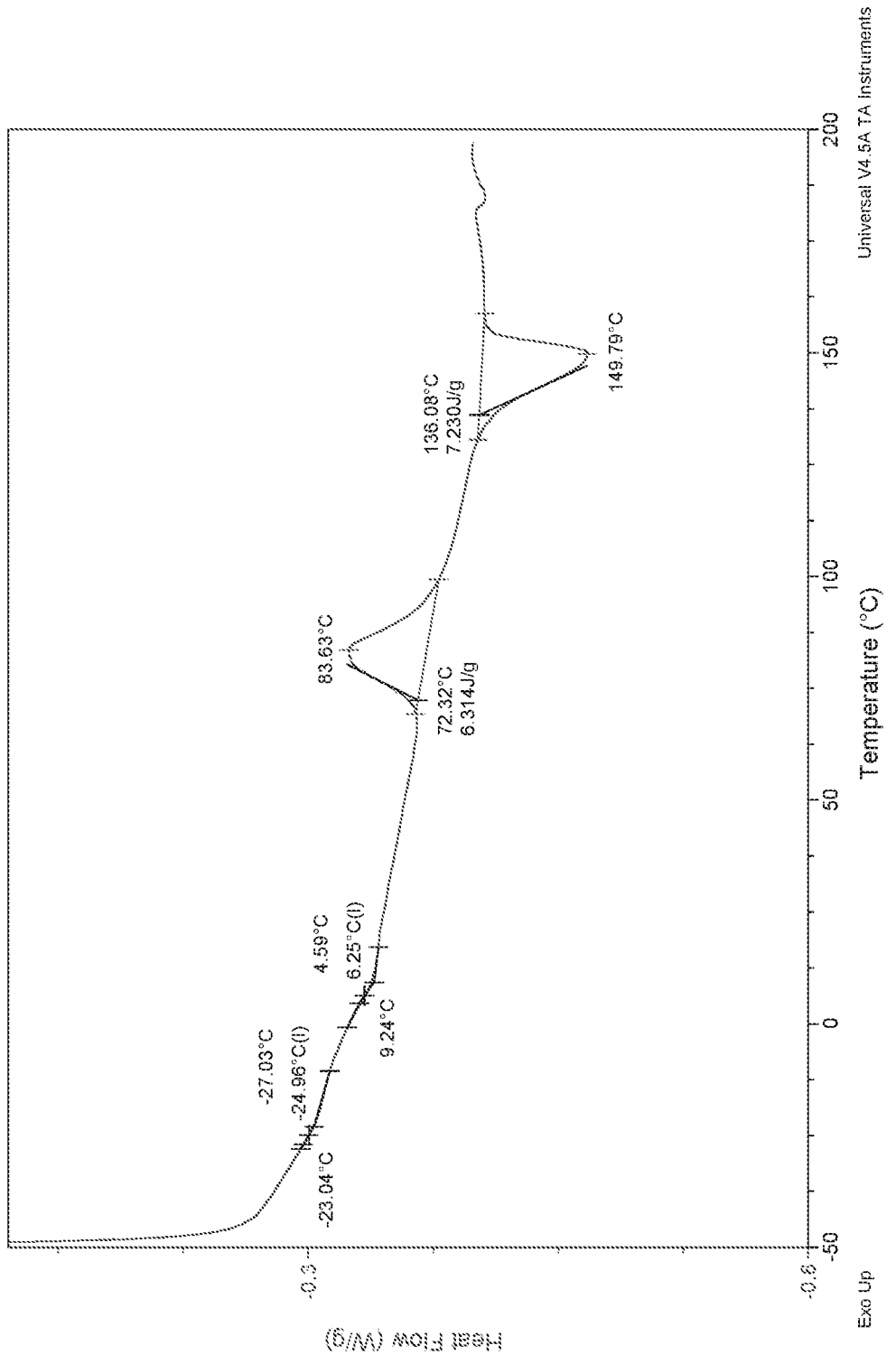
FIG. 8C is a DSC curve of a block copolymer including a polymer block of DEMM and a polymer block of MHMM. The block copolymer has two glass transition temperatures. The block copolymer also has a melting temperature, indicating the presence of a polymer block of diethyl methylene malonate. The Tg, Tc and Tm representative of poly (DEMM) block is lower than what would typically be observed for poly(DEMM) alone. This is attributed to the phase mixing of poly(DEMM) with poly(MHMM).

The molecular weight of the polymer may be measured using gel permeation chromatography (i.e., GPC), as shown in FIGS. 5A, 5B, 5C, 5D, and 6. FIG. 6, illustrates a GPC curve for a homopolymer prepared by polymerizing diethyl methylene malonate in an emulsion system. The reaction was continued until about 100 percent of the monomer was converted to polymer. This sample has a single peak which defines an area 50 for calculating the molecular weight characteristics of the polymer (e.g., weight average molecular weight, peak molecular weight, number average molecular weight, z-average molecular weight, and polydispsersity index). The GPC curve 58 shows the signal intensity (which correlates with concentration) as a function of the retention time in minutes. An example of a calibration curve 54 is also shown in FIG. 6. The calibration curve shows the retention time for a series of PMMA standards of known molecular weight. The low limit 56 for measuring the molecular weight based on this method with these standards is about 200 daltons. The polymer of diethyl methylene malonate characterized in FIG. 6 has a number average molecular weight of about 747, a weight average molecular weight of about 943, and a polydispersity index (i.e., Mw/Mn) of about 1.26. FIGS. 5A, 5B, 5C, and 5D illustrate the sequential increase in molecular weight when preparing a block copolymer.

FIG. 5A is measured after the first block is prepared, FIG. 5B is measured after the polymerization is continued for prepare a second polymer block. FIGS. 5C and 5D are measured after sequential polymerization of a third polymer block and a fourth polymer block respectively.

The polymer according to the teachings herein may be characterized as an elastomer. For example, the polymer may be substantially free of a melting temperature (e.g., a crystallinity of about 5% or less, or 3% or less, or 1% or less, or free of a melting temperature of about 15° C. or more) and free of a glass transition temperature of about 15° C. or more.

The polymer according to the teaching herein may be characterized as a thermoplastic having a melting temperature and/or a glass transition temperature of about 15° C. or more, about 50° C. or more, about 80° C. or more, about 100° C. or more, or about 120° C. or more. Polymers having a high glass transition temperature include those having bulky hydrocarbonyl groups that provide steric hindrance that reduce the mobility of polymer molecules in the amorphous state. The melting temperature and/or the glass transition temperature of the thermoplastic may be about 250° C. or less, about 200° C. or less, or about 150° C. or less.

The polymer may include one or more high temperature glass transition monomers, one or more low glass transition temperature monomers, or both. As used herein, "a high glass transition temperature monomer" and "a low glass transition temperature monomer" refers to the maximum glass transition temperature of a homopolymer prepared from the monomer and may be estimated by the glass transition of a homopolymer having a molecular weight of about 50,000 Daltons or more. For example, the polymer may be a copolymer including a first monomer and a second monomer, wherein the first monomer includes one or more 1,1-disubstituted alkene monomers that are high glass transition temperature monomers. The second monomer may include one or more low glass transition temperature monomers.

The polymer may be a block copolymer having a first polymer block including one or more high glass transition temperature monomers. For example, the amount of the high glass transition temperature monomer in the first polymer block may be sufficient so that the first polymer block is characterized by a glass transition temperature or melting temperature of about 15° C. or more (e.g., about 25° C. or more, about 35° C. or more, about 50° C. or more, about 80° C. or more, or about 100° C. or more). The high glass transition temperature monomer preferably includes, consists essentially of, or consists entirely of one or more 1,1-disubstituted alkene monomers.

The block copolymer may have a second polymer block including one or more low glass transition temperature monomers. The concentration of the low glass transition temperature monomers in the second polymer block preferably is sufficiently high so that the second polymer block is characterized as having no melting temperature above 15° C. and having a glass transition temperature of less than 15° C. (e.g., about 10° C. or less, about 0° C. or less, or about −20° C. or less). The low glass transition temperature monomer preferably includes, consists essentially of, or consists entirely of one or more 1,1-disubstituted alkene monomers.

The high glass transition temperature monomer may include one or more hydrocarbyl groups that result in polymers having high glass transition temperatures. For example, hydrocarbyl groups the presence of which result in polymers having generally high glass transition temperatures include aryl groups, aralkyl groups, alkaryl groups with the aryl group bonded to the 1 carbon atom, cycloalkyl groups, alkyl groups with a cycloalkyl group on the 1 carbon atom, or branched alkyl groups wherein the 1 carbon atom is a tertiary or the 1 and 2 carbon atoms are secondary. In certain embodiments the hydrocarbyl groups the presence of which increase the Tg of polymers formed therefrom include a cyclic terpene, alkyl substituted cycloalkyl, adamantyl, furfuryl, tertiary butyl groups, or mixtures thereof. In certain embodiments the hydrocarbyl groups the presence of which increase the Tg of polymers formed therefrom include fenchyl, menthyl, cyclohexyl, 2-phenyl propyl, or isobornyl groups. Exemplary 1,1-disubstituted alkenes having one or more hydrocarbyl groups on the carbonyl carbons which increase the glass transition temperatures of polymers prepared therefrom are illustrated by Formulas 1 and 2 presented hereinbefore. In certain embodiments the substituents on the hydrocarbyl groups on the 1,1-disubstituted alkenes may include alkyl, halo, alkoxy, alkylthio, hydroxyl, nitro, cyano, azido, carboxy, acyloxy, and sulfonyl groups; more preferred substituents include alkyl, halo, alkoxy, alkylthio, and hydroxyl groups, with halo, alkyl and alkoxy are even more preferred. In certain embodiments $R^1$ is separately in each occurrence $C_{4-15}$ branched chain alkyl wherein the 1 carbon atom is a tertiary or the 1 and 2 carbon atoms are secondary, $C_{4-15}$ branched chain alkenyl wherein the 1 carbon atom is a tertiary or the 1 and 2 carbon atoms are secondary, $C_{5-18}$ cycloalkyl, $C_{6-24}$ alkyl substituted cycloalkyl, $C_{4-18}$ aryl, $C_{4-20}$ aralkyl or $C_{4-20}$ alkaryl groups. In certain embodiments $R^1$ is separately in each occurrence $C_{4-8}$ branched chain alkyl wherein the 1 carbon atom is a tertiary or the 1 and 2 carbon atoms are secondary, $C_{5-12}$ cycloalkyl, $C_{6-12}$ alkyl substituted cycloalkyl, $C_{4-18}$ aryl, $C_{4-20}$ aralkyl or $C_{4-20}$ alkaryl groups. In certain embodiments $R^1$ is separately in each occurrence tertiary butyl, fenchyl, menthyl, cyclohexyl, 2-phenyl propyl, furfuryl, adamantyl and isobornyl.

The high glass transition temperature 1,1-disubstituted alkene monomers may include, consist essentially of, or consist entirely of one or more monomers selected from the group consisting of diethyl methylene malonate, dimethyl methylene malonate, phenylpropyl methyl methylene malonate, fenchyl methyl methylene malonate, fenchyl ethyl methylene malonate, menthyl ethyl methylene malonate, phenyl propyl ethyl methylene malonate, dicyclohexyl methylene malonate, cyclohexyl ethyl methylene malonate, isobornyl ethyl methylene malonate, benzyl ethyl methylene malonate, benzyl methyl methylene malonate, and dibenzyl methylene malonate. Preferably, the first polymer block includes about 50 weight percent or more (more preferably about 80 weight percent or more, and most preferably about 90 weight percent or more) of one or more monomers selected from the group consisting of diethyl methylene malonate, dimethyl methylene malonate, phenylpropyl methyl methylene malonate, fenchyl methyl methylene malonate, fenchyl ethyl methylene malonate, menthyl ethyl methylene malonate, phenyl propyl ethyl methylene malonate, dicyclohexyl methylene malonate, cyclohexyl ethyl methylene malonate, isobornyl ethyl methylene malonate, benzyl ethyl methylene malonate, benzyl methyl methylene malonate, dibenzyl methylene malonate, and any combination thereof.

The low glass transition temperature monomer may include hydrocarbyl groups that generally result in polymers having low glass transition temperatures. In some embodiments it may be desirable that such hydrocarbyl groups if homo-polymerized, prepare polymers having a glass transition temperature of no more than 15° C. (e.g., no more than 0° C.). Exemplary hydrocarbyl groups that meet these criteria include occurrence alkyl with a primary 1 carbon atom atom or a secondary 1 carbon atom and primary 2 carbon atom, alkenyl with a primary 1 carbon atom atom or a secondary 1 carbon atom and primary 2 carbon atom, alkaryl wherein the aryl group is bonded to a carbon atom which is 3 or more carbon atoms from X, alkyl group with a cycloalkyl group bonded to a carbon atom which is 3 or more carbon atoms from the X, or a polyalkylene ether. In some embodiments such hydrocarbyl groups include straight chain $C_{1-8}$ alkyl groups with a primary 1 carbon atom atom or a secondary 1 carbon atom and primary 2 carbon atom, straight chain $C_{1-8}$ alkenyl groups with a primary 1 carbon atom atom or a secondary 1 carbon atom and primary 2 carbon atom, alkoxy groups, polyalkylene ether groups and the like. In certain embodiments the hydrocarbyl groups may be methyl or ethyl. In formulas 1 to 3, preferably $R^2$ is separately in each occurrence alkyl with a primary 1 carbon atom atom or a secondary 1 carbon atom and primary 2 carbon atom, alkenyl with a primary 1 carbon atom atom or a secondary 1 carbon atom and primary 2 carbon atom, alkaryl wherein the aryl group is bonded to a carbon atom which is 3 or more carbon atoms from X, alkyl group with a cycloalkyl group bonded to a carbon atom which is 3 or more carbon atoms from the X, or a polyalkylene ether. In some embodiments $R^2$ is separately in each occurrence straight chain $C_{1-8}$ alkyl groups with a primary 1 carbon atom atom or a secondary 1 carbon atom and primary 2 carbon atom, straight chain $C_{1-8}$ alkenyl groups with a primary 1 carbon atom atom or a secondary 1 carbon atom and primary 2 carbon atom, alkoxy groups, polyalkylene ether groups and the like. In some embodiments $R^2$ is separately in each occurrence methyl or ethyl.

The low glass transition temperature 1,1-disubstituted alkene monomers may include, consist essentially of, or consist entirely of one or more monomers selected from the group consisting of methylmethoxy ethyl methylene malonate, ethylethoxy ethyl methylene malonate, hexyl methyl methylene malonate, dibutyl methylene malonate, dihexyl methylene malonate, hexyl ethyl methylene malonate, pentyl ethyl methylene malonate and dipentyl methylene malonate. Preferably, the second polymer block includes about 50 weight percent or more (more preferably about 80 weight percent or more, and most preferably about 90 weight percent or more) of one or more monomers selected from the group consisting of methylmethoxy ethyl methylene malonate, ethylethoxy ethyl methylene malonate, hexyl methyl methylene malonate, dibutyl methylene malonate, dihexyl methylene malonate, hexyl ethyl methylene malonate, pentyl ethyl methylene malonate, dipentyl methylene malonate, and any combination thereof.

It will be appreciated that a polymer or a polymer block having a high glass transition temperature may include one or more low glass transition temperature monomers in addition to the one or more high glass transition temperature. The amount of the low glass transition temperature monomer in such a polymer or polymer block should be sufficiently low that the glass transition temperature of the polymer or polymer block is about 25° C. or more, about 35° C. or more, about 50° C. or more, about 80° C. or more, about 100° C. or more, or about 120° C. or more. The amount of the low glass transition temperature monomer in such a block may be affected by the glass transition temperature(s) of the high glass transition temperature monomers in the polymer/polymer block. Preferably, the total concentration of low glass transition temperature monomer in such a polymer/polymer block is about 30 weight percent or less, about 20 weight percent or less, about 10 weight percent or less, or about 5 weight percent or less.

The block copolymer according to the teachings herein may include two or more polymer blocks. For example, the block copolymer may have, 2, 3, 4, 5, or more blocks. Adjacent polymer blocks (e.g., A blocks, B blocks, and optionally additional blocks) have different monomers, different concentration of monomers, or both. Each polymer block preferably has a degree of polymerization of about 15 or more, more preferably about 30 or more, and most preferably about 50 or more. The block copolymer may be a diblock copolymer or a triblock copolymer. The block copolymer include one or more A blocks and or more B blocks. The blocks may be connected at the ends of the blocks or one block may be placed along the length of the other block. For example, the block copolymer may have one or more of the following structures: A-B, A-B-A, B-A-B, A-B-A-B, A-B-A-B-A, or B-A-B-A-B. The block copolymer may be include a C block different from the A blocks and the B blocks. For example, the block copolymer may include or consist of the following block structure: A-B-C, A-C-B, or C-A-B.

The block copolymer may include polymer blocks that are not miscible so that the block copolymer has multiple phases at room temperature. As such, the block copolymer may have a first glass transition temperature corresponding to the first polymer block and a second glass transition temperature corresponding to the second polymer block. It will be appreciated that the glass transition temperature of the blocks may be tailored based on the monomer or monomers used in the particular block and/or based on end effects (which includes the effect of the number of monomer units in the block). For purposes of illustration, a polymer block consisting essentially of, or consisting entirely of: (1) diethyl methylene malonate homopolymer is expected to have a glass transition temperature of about 25° C. to about 45° C. (preferably about 30° C.), (2) fenchyl methyl methylene malonate is expected to have a glass transition temperature of about 145° C. to about 195° C. (preferably about 151° C.), (3) methyl methoxyethyl methylene malonate is expected to have a glass transition temperature of about −15° C. to about +10° C. (preferably about 0° C.), (4) hexyl methyl methylene malonate is expected to have a glass transition temperature of about −20° C. to about 10° C. (preferably about −5° C.), (5) dihexyl methylene malonate is expected to have a glass transition temperature of about −55° C. to about −35° C. (preferably about −44° C.). It may be possible to prepare a block copolymer having multiple glass transition temperatures, such as a first glass transition temperature characteristic of a first polymer block and a second glass transition temperature characteristic of a second polymer block. In some block copolymers, a single glass transition is observed indicating that a single phase is formed, indicating that the two polymer blocks have substantially the same glass transition temperature (e.g., a difference of about 20° C. or less, or about 10° C. or less), or both.

The block copolymer may include a block having a sufficient concentration of one or more high glass transition temperature monomer(s) (e.g., high glass transition temperature 1,1-disubstituted alkene monomer(s)) so that the block copolymer includes a high glass transition temperature block characterized by a glass transition temperature of about 25° C. or more (preferably about 50° C. or more). The high glass transition temperature block preferably has a glass transition temperature of about 250° C. or less or about 200° C. or less. The block copolymer may include a block having a sufficient concentration of one or more low glass transition temperature monomer(s) (e.g., low glass transition temperature 1,1-disubstituted alkene monomer(s)) so that the block copolymer includes a low glass transition temperature block characterized by a glass transition temperature of about 15° C. or less (preferably about 0° C. or less). The low glass transition temperature block preferably has a glass transition temperature of about −100° C. or more or about −80° C. or more.

The copolymers (e.g., the random copolymer or the block copolymer) according to the teachings herein include about 2 weight percent to about 98 weight percent of a first monomer and about 2 weight percent to about 98 weight percent of a second monomer, wherein the first monomer includes one or more 1,1-disubstituted alkene monomers (preferably one or more 1,1-dibstituted ethylene monomers). The copolymer may include one or more additional monomers. It will be appreciated that the second monomer and/or an additional monomer may be a 1,1-disubstituted alkene monomer or may be a monomer that is not a 1,1-disubstituted alkene monomer. The total concentration of 1,1-disubstituted alkene monomer(s) in the copolymer may be about 30 weight percent or more, about 50 weight percent or more, or about 70 weight percent or more, based on the total weight of the copolymer. In some embodiments, the copolymer consists substantially of, or entirely of 1,1-disubstituted alkene monomers. For example, the total concentration of 1,1-disubstituted alkene monomers in the copolymer may be about 80 weight percent or more, about 90 weight percent or more, about 95 weight percent or more, about 98 weight percent or more, or about 99 weight percent or more, based on the total weight of the copolymer. The first monomer preferably is present at a concentration of about 10 weight percent or more (e.g., about 20 weight percent or more, about 25 weight percent or more, about 30 weight percent or more, about 40 weight percent or more, about 50 weight percent or more, or about 60 weight percent or more based on the total weight of the copolymer. The first monomer preferably is present at a concentration of about 95 weight percent or less, more preferably about 90 weight percent or less, even more preferably about 85 weight percent or less, and most preferably about 80 weight percent or less, based on the total weight of the copolymer. The second monomer preferably is present at a concentration of about 5 weight percent or more, more preferably about 10 weight percent or more, even more preferably about 15 weight percent or more, and most preferably about 20 weight percent or more, based on the total weight of the copolymer. The second monomer preferably is present at a concentration of about 90 weight percent or less (e.g., about 80 weight percent or less, about 75 weight percent or less, about 60 weight percent or less, about 50 weight percent or less, or about 40 weight percent or less), based on the total weight of the copolymer. The first monomer may include or consist essentially of one or more high glass transition temperature monomers according to the teachings herein. The second monomer may include, consist essentially of, or consist entirely of one or more low glass transition temperature monomers according to the teachings herein.

The random copolymers including a first monomer and a second monomer according to the teachings herein preferably have a single glass transition temperature (e.g., even when a mixture of a homopolymer of the first monomer and a homopolymer of the second monomer, at the same concentration, exhibits multiple glass transition temperatures). A homopolymer may have a single glass transition temperature, such as illustrated in FIG. 2 for a homopolymer of 2-phenyl-1-propyl ethyl methylene malonate (Tg of about 59.4° C.) and FIG. 3 for a homopolymer of fenchyl methyl methylene malonate (Tg of about 146.9° C.). A random copolymer (of monomer A and monomer B) may have one or more glass transition temperatures (preferably a single glass transition temperature) between the glass transitions of the corresponding homopolymer (homopolymer A and homopolymer B), such as illustrated in FIG. 4, a random copolymer of 2-phenyl-1-propyl ethyl methylene malonate (about 50 weight percent) and fenchyl methyl methylene malonate (about 50 weight percent) having a single glass transition temperature of about 86.3° C.

The polymer according to the teachings herein may be a random copolymer and/or a block copolymer having a polymer block that is a random copolymer. The random copolymer may include a primary monomer (e.g., present at a concentration of about 50 mole percent or more) and a secondary monomer randomly distributed through the polymer chain and having a concentration of less than 50 mole percent. The properties of the random copolymer will generally differ from the properties of a homopolymer consisting entirely of the primary monomer. For example, as the amount of the secondary monomer is increased from about 0.5 mole percent to about 49.5 mole percent, the glass transition temperature of the random copolymer may shift from a glass transition temperature characteristic of the primary monomer towards a glass transition temperature characteristic of the secondary monomer. When prepared as a random copolymer, the polymer typically has a single glass transition temperature (e.g., even when a mixture of a homopolymer of the primary monomer and a homopolymer of the secondary monomer, at the same concentration, exhibits multiple glass transition temperatures).

The polymer or polymer block according to the teachings herein may include a primary monomer (i.e., a monomer present at a concentration of about 50 weight percent or more, based on the total weight of the polymer or of the polymer block). The primary monomer may be present at a concentration of about 60 weight percent or more, about 70 weight percent more, or about 80 weight percent or more, or about 90 weight percent or more, based on the total weight of the polymer and/or the total weight of the polymer block. The polymer or polymer block may include one or more secondary monomers (i.e., a monomer present at a concentration of less than 50 weight percent, based on the total weight of the polymer, based on the total weight of the polymer block, or both.

The homopolymer of the primary monomer may be a semicrystalline polymer. Typically, when a secondary monomer is added in preparing a random copolymer (or a polymer block that is a random copolymer), the secondary monomer will at least partially inhibit the ability of the primary monomer to crystallize, resulting in a random copolymer having different properties from the homopolymer such as a lower crystallinity, a lower flexural modulus, a lower melting temperature, or any combination thereof. For example, the selection of the secondary monomer and/or the amount of the secondary monomer in the random copolymer may be done so that the random copolymer has a melting temperature that is reduced (i.e., relative to the homopolymer of the primary monomer) by about 5° C. or more, by about 10° C. or more, by about 15° C. or more, or by about 20° C. or more. The selection of the secondary monomer and/or the amount of the secondary monomer in the random copolymer may be done so that the random copolymer has a crystallintity that is reduced (i.e., relative to the homopolymer of the primary monomer) by about 10% or more, by about 20% or more, by 40% or more, or by about 60% or more.

The polymer may be a block copolymer including at least a first polymer block and a second polymer block different from the first polymer block. The first polymer block and the second polymer block may differ with respect to one or any combination of the following properties: peak melting temperature, final melting temperature, crystallinity, glass transition temperature, flexural modulus, tensile modulus, elongation at failure, gas barrier properties, or adhesion properties. For example, the first polymer block and the second polymer block may have melting temperatures (peak melting temperatures and/or final melting temperatures) differing by about 10° C. or more, about 20° C. or more, about 30° C. or more, or about 50° C. or more. It will be appreciated that one polymer block may have a melting temperature and the other polymer block may be free of crystalline polymer so that there is no measurable melting temperature. The first polymer block and the second polymer block may have glass transition temperatures differing by about 10° C. or more, about 20° C. or more, about 30° C. or more, or about 40° C. or more. The first polymer block and the second polymer block may have crystallinities that differ by about 10% or more, about 15% or more, about 20% or more, about 25% or more, or about 30% or more. The first polymer block and the second polymer block may have moduli (e.g., flex modulus, tensile modulus, or both) having a ratio of about 1.5 or more, about 2 or more, about 4 or more, about 8 or more, or about 15 or more. The first polymer block and the second polymer block may have a ratio of elongation at failure and/or a ratio of tensile strength of about 2 or more, about 3 or more, about 4 or more, or about 6 or more.

The degree of blockiness (i.e., the blockiness index, or BI) in a random copolymer may be calculated by the ratio of the concentration of diad fractions of a first monomer (e.g., a primary monomer that is a 1,1-disubstituted alkene compound) added to the second monomer f(M1–M2) plus the diad fractions of the second monomer added to the first monomer f(M2–M1) to the theoretical concentration of diad fractions for a statistical random copolymer $2X_{M1}(1-X_{M1})$, where $X_{M1}$ is the molar fraction of first monomer:

$$BI=(f(M1-M2)+f(M2-M1))/(2X_{M1}(1-X_{M2}))$$

By definition a true statistically random copolymer has a BI of one (1.0). Blocky random copolymers will have a lower concentration of M1–M2 and M2–M1 diad fractions, and BI will be less than 1.0. Block copolymers will have very low concentrations of M1–M2 and M2–M1 diad fractions and BI will be much less than 1 and approach zero. On the other end, alternating copolymers having $X_{M1} \geq 0.5$ will have $BI=1+(1/X_{M1})$. The concentration of the diad fractions and $X_{M1}$ may be measured using $^{13}C$ NMR spectroscopy, using analogous peak assignments and techniques described by Yi-Jun Huange et al. in "Random Copolymers of Propylene Oxide and Ethylene Oxide Prepared by Double Metal Cyanide Complex Catalyst", Chinese Journal of Polymer Science, 20:5, 2002, pages 453-459, incorporated herein by reference in its entirety.

Preferred random copolymers have a BI of about 0.60 or more, more preferably about 0.70 or more, even more preferably about 0.75 or more, even more preferably about 0.80 or more, even more preferably about 0.85 or more, even more preferably about 0.90 or more, and most preferably about 0.95 or more. Preferred random copolymers have a BI preferably less than about $1+(0.8/x_{M1})$, more preferably less than about $1+(0.5/x_{M1})$, even more preferably less than about $1+(0.25/x_{M1})$, and most preferably less than about $1+(0.10/x_{M1})$ where $x_{M1}$ is the molar fraction of primary monomer in the copolymer and $x_{M1}$ is at least 0.5.

In some embodiments, the homopolymer or random copolymer includes a sufficient concentration of one or more high glass transition temperature monomer (e.g., high glass transition temperature 1,1-disubstituted alkene monomer(s)) so that the polymer is a high glass transition temperature polymer characterized by a glass transition temperature of about 25° C. or more (preferably about 50° C. or more). The high glass transition temperature polymer preferably has a glass transition temperature of about 250° C. or less or about 200° C. or less.

In some embodiments, the homopolymer or random copolymer includes a sufficient concentration of one or more low glass transition temperature monomer(s) (e.g., low glass transition temperature 1,1-disubstituted alkene monomer(s)) so that the polymer is a low glass transition temperature polymer characterized by a glass transition temperature of about 15° C. or less (preferably about 0° C. or less). The low glass transition temperature polymer preferably has a glass transition temperature of about –100° C. or more or about –80° C. or more.

Combinations of two or more different 1,1-disubstituted alkene monomers may result in improvements in one or more of the following properties: lap shear strength (i.e., increased lap shear strength), setting time (i.e., reduced setting time), or durability (i.e., increased retention of lap shear strength after environmental exposure). By way of example, the combination of a first monomer having a slow setting time and a high lap shear strength with a second monomer having a fast setting time and a low lap shear strength, may result in a monomer composition having an improved combination of fast setting time and high lap shear strength. The setting time of the composition (.g., on a window glass substrate, or a cold rolled steel substrate having sodium pyruvate secondary initiator applied) preferably is about 60 minutes or less, more preferably about 30 minutes or less, even more preferably about 10 minutes or less, and most preferably about 1 minute or less. The lap shear strength after 24 hours cure at room temperature on a window glass substrate, preferably is about 1 MPa or more, more preferably about 1.4 MPa or more, and most preferably about 1.6 MPa or more. The lap shear strength after curing for 24 hours at room temperature on a cold rolled steel substrate having sodium pyruvate secondary initiator applied is preferably about 3 MPa or more, more preferably about 5 MPa or more, even more preferably about 6 MPa or more, and most preferably about 8 MPa or more. The lap shear strength after curing for 72 hours at room temperature on a cold rolled steel substrate having sodium pyruvate secondary initiator applied is preferably about 8 MPa or more, more preferably about 8.5 MPa or more, even more preferably about 9 MPa or more, and most preferably about 9.5 MPa or more.

Lap shear strength samples are prepared generally according to ASTM D1002 (with the shear strength measured on an Instron at a rate of 50 mm/min) using various polymeric compositions including about 97 weight percent or more of one or more 1,1-disubstituted alkenes monomers. The lap shear strength was measured after curing for 1 hour, 24 hours, and 72 hours at room temperature. Some specimens that were cured for 72 hours were then tested for durability in boiling water for about 60-90 minutes or for durability in a dishwasher environment after 10 cycles using water having a temperature of about 40° C. and common detergent. In some studies, a control using Loctite glass glue, a commercially sold glass bonding adhesive was employed. Lap shear samples are generally zero gap and the bond line is low. Setting time of the polymeric compositions is determined by the time for the composition to cure sufficiently to support a weight of about 4.54 kg for 10 seconds in shear.

In some embodiments, the polymer is a linear polymer that is free of long chain branching.

In some embodiments, the polymer includes long branching. For example, the polymer may have 1, 2, 3, 4, 5, 6, or more long chain branches. The amount of long chain branching may be sufficient so that one or more rheological properties is significantly affected (e.g., zero shear viscosity in solution, zero shear viscosity of the bulk polymer, melt viscosity, or melt flow rate). For example, the melt flow rate (as measured according to ASTM D1238) of the polymer including the long chain branching may be changed by 10% or more, or 25% or more, compared with a linear polymer having the same monomers and the same total molecular weight. A long chain branch may have a length of about 3 or more monomer units, preferably about 10 or more monomer units. A long chain branch may be a branch from a side of the backbone of a chain. A long chain branch may be formed when initiating and/or terminating a polymer reaction. A polymer including long chain branching may be a star polymer including 3, 4, 5, 6, 7 or more arms connected at a central location. For example, the polymer may be prepared using a polyfunctional nucleophile. Preferred star polymers have arms that are about the same length. For example, the star polymer may have two arms having molecular weights that differ by less than about 50%, preferably that differ by less than about 30%, or differ by less than about 20%.

Figure 9:
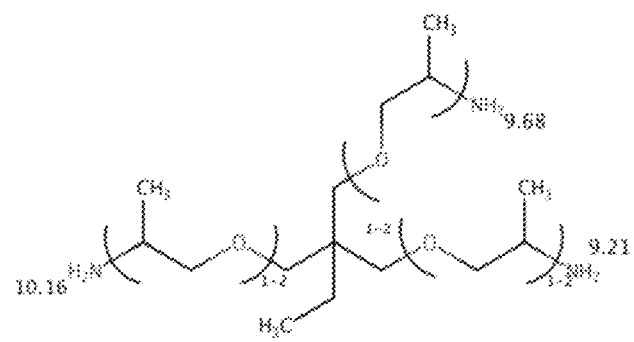
FIG. 9 is a drawing illustrating a structure of a multifunctional amine initiator. The drawing is a representative structure of JEFFAMINE 403 and shows the illustrative pKa values of the multiple initiation sites.

Long chain branching may be formed during initiation of the polymer, during propogation of the polymer (e.g., using small concentrations of a suitable multi-functional monomer), or during a termination reaction. As illustrated in FIG. 9, long chain branching may be formed using a multifunctional initiator. For example, the multifunctional initiator may be a multifunctional amine, such as a JEFFAMINE 403.

Long chain branching may also be formed using a multifunctional terminator. The multifunction terminator may be any terminator capable of reacting with a plurality of reactive chain ends. By way of example the multifunctional terminator may be a multifunctional silane, such as tetrachlorosilane. It will be appreciated that by employing a multifunctional initiator and a multifunctional terminator, the termination step may result in cross-linking of the polymer.

The polymer may be employed in a polymeric composition including one or more additives, such as antioxidants, heat stabilizers, light stabilizers, process stabilizers, lubricants, antiblocking agents, antistatic agent, anti-fogging agents, solvents, plasticizers, fillers, antistatic agents, coupling agents (e.g., for the fillers), crosslinking agents, nucleating agent, anti-blocking agent, defoaming agents, pigments, colorant, flame retardant additives, flow aid, lubricant, slip agent and other processing aids known to the polymer compounding art. Suitable flame retardants may include halogen containing flame retardants and halogen free flame retardants.

Polymeric compositions may comprise one or more other fillers, such as a filler particle (e.g., fibers, powders, beads, flakes, granules, and the like). The filler particle may be a fiber (e.g., having an aspect ratio of the longest direction to each perpendicular direction that is greater than 10). The filler particle may be a particle that is not a fiber (e.g., having an aspect ratio of the longest direction to a perpendicular direction that is less than 10, less than 8, or less than 5). The filler may be formed of an organic material and/or an inorganic material. Examples of organic fillers include fillers derived from biomass and fillers derived from polymers. Inorganic fillers include, nonmetallic materials, metallic materials, and semiconductor material. For example, the filler particle may include alumina silicate, aluminum hydroxide, alumina, silicon oxide, barium sulfate, bentonite, boron nitride, calcium carbonate (e.g., activated calcium carbonate, light calcium carbonate, or heavy calcium carbonate), calcium hydroxide, calcium silicate, calcium sulfate, carbon black, clay, cotton flock, cork powder, diatomaceous earth, dolomite, ebonite powder, glass, graphite, hydrotalcite, iron oxide, iron metallic particles, kaolin, mica, magnesium carbonate, magnesium hydroxide, magnesium oxide, phosphide, pumice, pyrophyllite, sericite, silica, silicon carbide, talc, titanium oxide, wollastonite, zeolite, zirconium oxide, or any combination thereof. The filler particles may be present at a concentration of about 0.1 weight percent or more, about 1 weight percent or more, about 5 weight percent or more, or about 10 weigh percent or more. The filler particles may be present at a concentration of about 70 weight percent or less, about 50 weight percent or less, about 35 weight percent or less, or about 25 weigh percent or less. The filler particles preferably have one, two, or three dimensions that are about 1 mm or less, about 0.3 mm or less, about 0.1 mm, about 50 µm or less, about 10 µm or less. The filler particles preferably have one, two, or three dimensions that are about 0.1 µm or more, about 0.3 µm or more, or about 1 µm or more.

The polymeric compositions according to the teachings herein may include a plasticizer for adjusting the properties of the final polymer for the desired use. The plasticizer may be added prior to, during, or after polymerization. For example, in certain embodiments, a suitable plasticizer can be included with the 1,1-disubstituted alkene monomer. Generally, suitable plasticizers can include plasticizers used to modify the rheological properties of adhesive systems including, for example, straight and branched chain alkylphthalates such as diisononyl phthalate, dioctyl phthalate, and dibutyl phthalate, as well as partially hydrogenated terpene, trioctyl phosphate, epoxy plasticizers, toluene-sulfamide, chloroparaffins, adipic acid esters, sebacates such as dimethyl sebacate, castor oil, xylene, 1-methyl-2-pyrrolidione and toluene. Commercial plasticizers such as HB-40 manufactured by Solutia Inc. (St. Louis, Mo.) can also be suitable.

The polymer of the current teaching may be mixed with one or more additional polymers for preparing a polymeric composition. The concentration of the polymer in the polymeric composition may be about 1 weight percent or more, about 5 weight percent or more, about 10 weight percent or more, about 20 weight percent or more, or about 50 weight percent or more, based on the total weight of the polymers in the polymeric composition. The polymer may be present in the polymeric composition at a concentration of about 100 weight percent or less, about 95 weight percent or less, or about 90 weight percent or less, or about 60 weight percent or less, based on the total weight of the polymers in the polymeric composition.

The polymers and polymer compositions according to the teachings herein may have one or more rheological properties (e.g., melt index, melt flow rate, viscosity, melt strength, and the like) suitable for processing the polymer with known polymer processing equipment. For example, the polymer or polymer composition including 1,1-disubstituted alkene compounds may be processed using extrusion, co-extrusion, injection molding, insert molding, co-injection molding, calendaring (e.g., using two or more rolls), blow molding, compression molding, thermoforming, rolling, spray coating. For example, the polymeric material (i.e., the polymer or the polymer composition) may be fed through a processing apparatus having a screw and a barrel assembly wherein the polymeric material is conveyed along the screw at a temperature at which the polymeric material is at least partially in a liquid state (e.g., above any glass transition temperature and above any melting temperature).

The polymers according to the teachings herein preferably adhere to one or more of the following substrates: aluminum, steel, glass, silicon, or wood. For example, when separating two substrates having the polymer placed between the substrates, the separation of the substrates may result in cohesive failure of the polymer, where some polymer remains on the surfaces of the substrates.

The polymers and/or polymeric compositions according to the teaching herein may be packaged (e.g., as solid particles, or as a liquid) for storage and or transport.

The polymers and/or polymeric compositions according to the teachings herein may be employed in extruded, blow molded, injection molded, thermoformed, or compression molded articles, or applied as a coating or adhesive layer to a substrate. The polymer or polymeric composition may be employed as an adhesive. For example, the polymers may be employed in a pressure sensitive adhesive composition. The polymers may be employed as a coating, such as a protective coating. The polymer may be employed as a primer layer over a substrate. In some embodiments, a polymerizable composition including the one or more 1,1-disubstituted alkene monomers is applied to a substrate and a polymerization reaction occurs after the application of the polymerizable composition.

Melting temperatures and glass transition temperatures are measured using differential scanning calorimetry on a sample of about 0.5-1.0 mg. The sample is heated at a rate of about 10° C./min and then cooled at a rate of about 20° C./min.

The molecular weight is determined using gel permeation chromatography. GPC samples are prepared by dissolving the polymer in tetrahydrofuran (THF). About 25 uL of the dissolved polymer solution is injected into the THF eluent having a flow rate of 1 mL/min. Two columns with 5 micron, highly crosslinked polystyrene/divinylbenzene matrix particles are employed. These columns are designed to measure molecular weights of linear polymers from 200 to 2,000,000. The column pressure is about 65 bar and the column temperature is about 35° C. The elution time is 30 minutes. The column is calibrated using PMMA standards. As such, the units for molecular weight are relative based on the standard PMMA equivalent molecular weights.

Monomer conversion is calculated using quantitative NMR. A 300 MHz NMR is employed. Any residual polymerization reaction of the emulsion polymerization specimen is quenched prior to NMR analysis by adding trifluoroacetic acid. The preferred solvent is DMSO-d6 as it is a polar aprotic solvent. When the solvent is added to the emulsion, the aqueous and non-aqueous phases become miscible. Acetic acid is added as an internal standard and is suitable for these monomer compositions. The double bond intensity at about 6.45 ppm is measured to determine the concentration of unconverted monomer. This double bond is a singlet for symmetrical monomers such as diethyl methylene malonate and dibutyl methylene malonate, and it is a doublet for asymmetrical monomers such as hexyl methyl methylene malonate. Four NMR scans are run on each specimen with a 20 second delay between scans.

Unless otherwise specified, crystallinity and melting temperature are measured according to ASTM D3418-15 at a heating rate of about 10° C./min.

Unless otherwise specified, glass transition temperatures are measured according to ASTM D3418-15 at a heating rate of about 20° C./min.

Unless otherwise specified, solution viscosity is measured according to ASTM D5225.

Unless otherwise specified, the dynamic viscosity and the kinematic viscosity of the polymer is measured according to ASTM D445.

EXAMPLES

Examples 1 through 62 are polymers prepared using emulsion polymerization processes as described in U.S. patent application Ser. No. 14/789,178 filed on Jul. 1, 2015, (see e.g., paragraphs 96 through 135 and tables 1-7, incorporated herein by reference). Unless otherwise specified, all monomers are high purity monomers having a purity of about 97 mole percent or more; a concentration of impurity including a dioxane of about 0.05 mole percent or less, and about 0.1 mole percent or less of an analogous impurity having the alkene group replaced with a hydroxyalkyl group.

Example 1 is a polymer prepared by anionic emulsion polymerization of a high purity diethyl methylene malonate at a temperature of about 23° C. The polymer is characterized using gel permeation chromatography. The GPC is calibrated using PMMA standards and is used to measure the molecular weight distribution of the polymer. Example 1 has a number average molecular weight of about 15,579, a weight average molecular weight of about 21,010, and a polydispersity index of about 1.36.

Examples 2-6 are prepared similar to Example 1, except the ratio of monomer to activator and/or the type of activator are changed.

The molecular weight distributions of Examples 1 through 6 are shown in the Table 1.

TABLE 1

|  | Example 1 | Example 2 | Example 3 | Example 4 | Example 5 | Example 6 |
|---|---|---|---|---|---|---|
| Activator |  |  |  |  |  |  |
| Sodium Benzoate | X | X | X |  |  |  |
| 1,1,3,3-Tetramethylguanidine |  |  |  | X |  |  |
| Pyridine |  |  |  |  | X |  |
| Sodium Silicate |  |  |  |  |  | X |
| Ratio of monomer to activator | 500:1 | 1000:1 | 100:1 | 100:1 | 100:1 | 100:1 |
| Polymer Properties |  |  |  |  |  |  |
| Conversion of monomer to polymer | >99.9% | >99.9% | >99.9% | >99.9% | >99.9% | >99.9% |
| Number average molecular weight | 15,579 | 55,031 | 747 | 1,173 | 991 | 1,289 |
| Weight average molecular weight | 21,010 | 71,022 | 943 | 1,582 | 1,334 | 1,724 |
| Polydispersity Index | 1.36 | 1.29 | 1.26 | 1.26 | 1.35 | 1.34 |

Examples 7-12 are polymer prepared by anionic emulsion polymerization of a high purity diethyl methylene malonate at a temperature of about 23° C. using different monomer to activator ratios. The conversion of monomer to polymer of about 100 percent. The molecular weight characterization of Examples 7-12 are listed in Table 2.

TABLE 2

|  | Example 7 | Example 8 | Example 9 | Example 10 | Example 11 | Example 12 |
|---|---|---|---|---|---|---|
| Activator |  |  |  |  |  |  |
| Sodium Benzoate | X | X | X | X | X | X |
| Surfactant |  |  |  |  |  |  |
| SURFYNOL ® 485 | X | X | X | X | X | X |
| Ratio of monomer to activator | 1000:1 | 100:1 | 200:1 | 500:1 | 8000:1 | 16000:1 |
| Polymer Properties |  |  |  |  |  |  |
| Conversion of monomer to polymer | ≈100% | ≈100% | ≈100% | ≈100% | ≈100% | ≈100% |
| Number average molecular weight | 4,161 | 9,442 | 7,290 | 6,939 | 3104 | 1226 |
| Weight average molecular weight | 13,535 | 18,605 | 17,782 | 18,038 | 5411 | 2237 |
| Polydispersity Index | 3.25 | 2.5 | 2.43 | 2.60 | 1.94 | 1.82 |

Freeze/thaw stability is evaluated by first measuring the initial viscosity of the polymer specimen. The polymer specimen is then placed in a chamber at a temperature of about −24° C. for about 17 hours, and then to a room temperature of about 22° C. for about 7 hours. This 24 hour cycle is repeated 5 times. The viscosity of the specimen is measured after being at room temperature for about 7 hours. The specimen is also observed for any signs of settling, gelation, or coagulation which would indicate an instable emulsion system. Conversely, no observed signs of settling, gelation, or coagulation indicates a stable emulsion system.

Example 13 is a sample of poly (diethyl methylene malonate) (i.e., poly(DEMM)) having a number average molecular weight of about 995 and prepared by emulsion polymerization. The initial viscosity of Example 13 is about 10-22 cPs. After 5 freeze/thaw cycles, the specimen still has a viscosity of about 10-22 cPs. During the 5 cycles, there is no indication of settling, gelation, or coagulation.

Example 14 is a sample of poly (dibutyl methylene malonate) (i.e., poly(DBMM)) having a number average molecular weight of about 2121 and prepared by emulsion polymerization. The initial viscosity of Example 14 is about 13-24 cPs. After 5 freeze/thaw cycles, the specimen still has a viscosity of about 13-24 cPs. During the 5 cycles, there is no indication of settling, gelation, or coagulation.

Example 15 is a sample of poly (hexyl methyl methylene malonate) (i.e., poly(HMMM)) having a number average molecular weight of about 5018 and prepared by emulsion polymerization. The initial viscosity of Example 15 is about 15-25 cPs. After 5 freeze/thaw cycles, the specimen still has a viscosity of about 15-25 cPs. During the 5 cycles, there is no indication of settling, gelation, or coagulation.

Example 16 is a sample of poly(DEMM) having a number average molecular weight of about 25,000 prepared by emulsion polymerization. The polymer is tested for freeze/thaw stability. After 5 freeze/thaw cycles, Example 16 shows signs of settling, gelation and coagulation, and does not flow.

Examples 17, 18, 19, 20, and 21 are homopolymers of poly(DEMM) are prepared having number average molecular weight of 25,345 through 498,003, as shown in Table 3. About 0.05 weight percent of hydroxyethyl cellulose stabilizer is added to each of the polymer samples. After 5 freeze/thaw cycles, there is no evidence of settling, gelation, or coagulation, and the final viscosity is substantially unchanged from the initial viscosity.

TABLE 3

|  | Example 17 | Example 18 | Example 19 | Example 20 | Example 21 |
|---|---|---|---|---|---|
| Number Average Molecular Weight | 25,345 | 50,989 | 125,129 | 209,039 | 498,003 |
| Initial Viscosity, cPs | 9 to 22 | 10 to 24 | 10 to 20 | 10 to 24 | 15 to 25 |
| Viscosity after 5 freeze/thaw cycles | 11 to 25 | 12 to 24 | 10 to 20 | 12 to 24 | 12 to 23 |
| Settling/Gelation/Coagulation after 5 freeze/thaw cycles | None | None | None | None | None |

Examples 22, 23, 24, 26, 26, 27, 28, and 29 are prepared by anionic emulsion polymerization using different surfactant mixtures at about 23° C. The surfactant and amount of surfactant for each Example is shown in Table 4. The activator is sodium benzoate and is added at a monomer to activator ratio of about 100:1. The approximate times for 95% and 99% conversion of monomer to polymer (as measured using quantitative NMR spectroscopy) is listed in Table 4. The reaction is continued for 4 hours. The final conversion is also listed in Table 4. Although addition of DBSA may retard the reaction rate, addition of small amounts of DBSA (e.g., less than about 1500 ppm) may results in a high polymerization reaction rate and polymers having a narrow molecular weight distribution.

TABLE 4

|  | Example 22 | Example 23 | Example 24 | Example 25 | Example 26 | Example 27 | Example 28 | Example 29 |
|---|---|---|---|---|---|---|---|---|
| Surfynol 485 | 2 wt. % | 2 wt. % | 2 wt. % | 2 wt. % | 2 wt. % | 2 wt. % | 2 wt. % | 0 wt. % |
| DBSA, ppm | 0 | 500 | 1000 | 2000 | 3000 | 4000 | 5000 | 5000 |
| Number average molecular weight | 6939 | 14109 | 2756 | 931 | 721 | 687 | 764 | 15579 |
| Weight average molecular weight | 18038 | 17258 | 4104 | 1150 | 908 | 904 | 950 | 21010 |
| Polydispersity Index | 2.60 | 1.22 | 1.49 | 1.24 | 1.26 | 1.32 | 1.24 | 1.35 |
| Monomer Conversion, % (after 4 hours) | 99.98 | 99.99 | 99.99 | 99.32 | 98.83 | 89.73 | 89.03 | 16.92 |
| Time for 95% conversion (min) | <1 | ≈4 | ≈6 | ≈250 | ≈300 | >480 | >480 | >480 |
| Time for 99% conversion (min) | ≈7 | ≈7 | ≈8 | ≈400 | >480 | >480 | >480 | >480 |

Example 30 is a homopolymer prepared via emulsion polymerization using diethyl methyl malonate at about 23° C. The molar ratio of diethyl methylene malonate monomer to sodium benzoate is about 200:1. The reaction time is about 10 minutes and the conversion of the monomer to polymer is greater than 99.9%. The recovered polymer has a weight average molecular weight greater than 50,000 and a glass transition temperature of about 35° C.

Example 31 is a homopolymer prepared using the same procedure as for Example 30, except the diethyl methyl malonate monomer is replaced with fenchyl methyl methylene malonate monomer and the initiator is sodium silicate at a molar ratio of monomer to activator of about 200:1. The recovered polymer has a weight average molecular weight greater than 50,000 and a glass transition temperature of about 143° C.

Example 32 is a homopolymer prepared using the same procedure as for 30, except the diethyl methyl malonate monomer is replaced with methylmethoxy ethyl methylene malonate monomer and the initiator is sodium silicate at a molar ratio of monomer to activator of about 200:1. The recovered polymer has a weight average molecular weight greater than 50,000 and a glass transition temperature of about 0° C.

Example 33 is prepared using the same procedure as for Example 30, except the diethyl methyl malonate monomer is replaced with hexyl methyl methylene malonate monomer and the initiator is sodium silicate at a molar ratio of monomer to activator of about 200:1. The recovered polymer has a weight average molecular weight greater than 50,000 and a glass transition temperature of about −34° C.

Homopolymer Example 34 is prepared using the same procedure as for Example 30, except the diethyl methyl malonate monomer is replaced with dibutyl methylene malonate monomer and the surfactant is sodium silicate at a molar ratio of monomer to activator of about 200:1. The recovered polymer has a weight average molecular weight greater than 50,000 and a glass transition temperature of about −44° C.

Homopolymer Example 35 is prepared using the same procedure as for Example 30, except the molar ratio of the diethyl methylene malonate monomer to the sodium benzoate activator is about 100:1. In preparing Example 35, the solution is agitated using a mixing speed of about 400 rpm. The mixing time is about 1 hour. The resulting emulsion is measured using dynamic light scattering. The polymer particles have a refractive index of about 1.81. The number average particle size is about 28.6 μm with a standard deviation of about 7.6 μm. Homopolymer Example 36 is prepared using the same procedure as for Example 35, except the mixing speed was increased to about 1500 rpm. The resulting polymer particles have a refractive index of about 1.81, an average particle size of about 6.44 μm with a standard deviation of about 3.31 μm. Homopolymer Example 37 is prepared using the same procedure as for Example 35, except the agitation was achieved using sonication at a frequency of about 40 kHz. The resulting polymer particles have a refractive index of about 1.81, an average particle size of about 0.48 μm with a standard deviation of about 0.09 μm. The homopolymer results for H-1 through H-6 are summarized in Table 5.

TABLE 5

|  | Example 30 | Example 31 | Example 32 | Example 33 | Example 34 |
|---|---|---|---|---|---|
| Monomer Type of polymer | DEMM homoplymer | FMMM homoplymer | MMOEMM homoplymer | HMMM homoplymer | DBMM homoplymer |
| Weight average molecular weight, Mw | >50,000 | >50,000 | >50,000 | >50,000 | >50,000 |
| Glass Transition Temp., ° C. | 35 | 143 | 0 | −34 | −44 |
| Monomer conversion | >99.9% | >99.9% | >99.9% | >99.9% | >99.9% |

Example 38 is a mixture of two homopolymers, homopolymer Example 30 and homopolymer Example 31 are dissolved together in dichloromethane solvent at a weight ratio of the two homopolymers of 1:1. The polymer mixture is then precipitated from solution by adding methanol (at about −25° C.) at a volume of about 4 times the volume of the solvent. The precipitated polymer is further washed with a 1:1 mixture (by weight) of methanol and hexane (at about −25° C.). The resulting polymer mixture has two glass transition temperatures at about 45° C. and at about 137° C.

Example 39 is a mixture of two homopolymers, homopolymer Example 30 and homopolymer Example 32. The polymer mixture is prepared using the same method as described above for Example 38, except homopolymer Example 31 is replaced by homopolymer Example 32. The resulting polymer mixture has two glass transition temperatures at about 28° C. and at about 12° C.

Example 40 is a mixture of two homopolymers, homopolymer Example 30 and homopolymer Example 33. The polymer mixture is prepared using the same method as described above for Example 38, except homopolymer Example 31 is replaced by homopolymer Example 33. The resulting polymer mixture has two glass transition temperatures at about 25° C. and at about −25° C.

Example 41 is a mixture of two homopolymers, homopolymer Example 30 and homopolymer Example 34. The polymer mixture is prepared using the same method as described above for Example 38, except homopolymer Example 31 is replaced by homopolymer Example 34. The resulting polymer mixture has a single glass transition temperature at about −5° C.

Example 42 is a mixture of two homopolymers, homopolymer Example 31 and homopolymer Example 32. The polymer mixture is prepared using the same method as described above for Example 38, except homopolymer Example 30 is replaced by homopolymer Example 31, and homopolymer Example 31 is replaced by homopolymer Example 32. The resulting polymer mixture has two glass transition temperatures at about 131° C. and at about 10° C.

Example 43 is a mixture of two homopolymers, homopolymer Example 31 and homopolymer Example 33. The polymer mixture is prepared using the same method as described above for Example 38, except homopolymer Example 30 is replaced by homopolymer Example 31, and homopolymer Example 31 is replaced by homopolymer Example 33. The resulting polymer mixture has two glass transition temperatures at about 132° C. and at about −14° C.

Example 44 is a mixture of two homopolymers, homopolymer Example 31 and homopolymer Example 34. The polymer mixture is prepared using the same method as described above for Example 38, except homopolymer Example 30 is replaced by homopolymer Example 31, and homopolymer Example 31 is replaced by homopolymer Example 34. The resulting polymer mixture has two glass transition temperatures at about 129° C. and at about −33° C.

Example 45 is a mixture of two homopolymers, homopolymer of Example 32 and Example 33. The polymer mixture is prepared using the same method as described above for Example 38, except homopolymer Example 30 is replaced by homopolymer Example 32, and homopolymer Example 31 is replaced by homopolymer Example 33. The resulting polymer mixture has two glass transition temperatures at about −7° C. and at about −25° C.

Example 46 is a mixture of two homopolymers, homopolymers of Example 32 and Example 34. The polymer mixture is prepared using the same method as described above for Example 38, except homopolymer Example 30 is replaced by homopolymer Example 32, and homopolymer Example 31 is replaced by homopolymer Example 33. The resulting polymer mixture has two glass transition temperatures at about −9° C. and at about −36° C.

Example 47 is a mixture of two homopolymers, homopolymer Example 33 and homopolymer Example 34. The polymer mixture is prepared using the same method as described above for Example 38, except homopolymer Example 30 is replaced by homopolymer Example 33, and homopolymer Example 31 is replaced by homopolymer Example 34. The resulting polymer mixture has a single glass transition temperature at about −37° C.

Examples 48, 49, 50, 51, 52, 53, 54, 55, 56, and 57 are random copolymer prepared according to the method of Example 30 homopolymer, except the monomer of diethyl methyl malonate is replaced with a 1:1 weight ratio of monomer 1 and monomer 2, as listed in Table 6. The resulting polymers are random copolymers having a weight average molecular weight of 50,000 or more, and having a conversion of monomer to polymer of greater than 99.9 weight percent. Each of the random copolymers has a single glass transition temperature as shown in the Table 6.

TABLE 6

| Example Number | Monomer 1 | Monomer 2 | Glass Transition Temp, ° C. |
|---|---|---|---|
| Example 48 | Diethyl methylene malonate | fenchyl methyl methylene malonate | 88 |
| Example 49 | Diethyl methylene malonate | methylmethoxy ethyl methylene malonate | 17 |
| Example 50 | Diethyl methylene malonate | hexyl methyl methylene malonate | 1 |
| Example 51 | Diethyl methylene malonate | dibutyl methylene malonate | −4 |
| Example 52 | fenchyl methyl methylene malonate | methylmethoxy ethyl methylene malonate | 72 |
| Example 53 | fenchyl methyl methylene malonate | hexyl methyl methylene malonate | 55 |
| Example 54 | fenchyl methyl methylene malonate | dibutyl methylene malonate | 50 |
| Example 55 | methylmethoxy ethyl methylene malonate | hexyl methyl methylene malonate | −16 |
| Example 56 | methylmethoxy ethyl methylene malonate | dibutyl methylene malonate | −22 |
| Example 57 | hexyl methyl methylene malonate | dibutyl methylene malonate | −38 |

Example 58 is a block copolymer prepared by sequentially polymerizing a first polymer block, a second polymer block, and a third polymer block. The first polymer block is prepared as described above for homopolymer Example 30, except the amount of the monomer is reduced to about one-third of the monomer employed in Example 30. After preparing the first polymer block, a sample of the polymer (Example 58, stage 1) is removed, quenched with about 500 ppm of trifluoroacetic acid, precipitated, and washed for analysis, as described above. The remaining polymer is further polymerized by adding a second monomer (fenchyl methyl methylene malonate) to the emulsion to form a second polymer block consisting essentially of the second monomer. The amount of the second monomer is about one-third of the total monomer used in Example 30. After preparing the second polymer block, a sample of the diblock polymer (Example 58, stage 2) is removed, quenched with about 500 ppm trifluoroacetic acid, precipitated, and washed for analysis. The remaining polymer is further polymerized by adding an additional amount of the first monomer into the emulsion to polymerize a third polymer block consisting essentially of the first monomer. The amount of the third monomer is about one-third of the monomer employed in Example 30. The resulting tri-block copolymer (Example 58 stage 3) is quenched with about 500 ppm of trifluoroacetic acid, precipitated, and washed.

Examples 59, 60, and 61 are block copolymers prepared according to the method described above for Example 58, except the second monomer of fenchyl methyl methylene malonate is replaced with methylmethoxy ethyl methylene malonate, hexyl methyl methylene malonate, and dibutyl methylene malonate, respectively.

The properties of Examples 58, 59, 60, and 61 at the end of each of the three stages (single block, diblock, and triblock) are listed in Table 7.

TABLE 7

|  | Example 58 | Example 59 | Example 60 | Example 61 |
|---|---|---|---|---|
| After stage 1 (single block) | | | | |
| Monomer (first block) | DEMM | DEMM | DEMM | DEMM |
| Conversion, wt. % | >99.9 | >99.9 | >99.9 | >99.9 |
| Mn | 16167 | 16191 | 16103 | 16093 |
| Polydispersity Index | 1.3 | 1.3 | 1.3 | 1.3 |
| Glass Transition Temp, ° C. | 34 | 35 | 35 | 34 |
| After stage 2 (diblock) | | | | |
| Monomer (second block) | FMMM | MMOEMM | HMMM | DBMM |
| Conversion, wt. % | >99.8 | >99.9 | >99.9 | >99.8 |
| Mn | 29384 | 31903 | 30789 | 28263 |
| Polydispersity Index | 2.1 | 1.9 | 1.8 | 2.0 |
| Glass Transition Temp, ° C. | 48 and 132 | 8 and 27 | −26 and 23 | −8 |
| After stage 3 (triblock) | | | | |
| Monomer (third block) | DEMM | DEMM | DEMM | DEMM |
| Conversion, wt. % | >99.8 | >99.8 | >99.9 | >99.7 |
| Mn | 44102 | 45093 | 44387 | 42561 |
| Polydispersity Index | 2.9 | 2.4 | 2.2 | 2.6 |
| Glass Transition Temp, ° C. | 38 and 125 | 15 and 33 | −9 and 32 | 10 |

Example 62. A pressure sensitive adhesive emulsion composition is prepared by mixing about 67.98 parts deionized water, about 0.03 parts 4-dodecylbenzenesulfonic acid, and about 2.00 parts ethoxylated 2,4,7,9-tetramethyl-5-decyne-4,7-diol at about 700 rpm. A 10% solution of sodium silicate activator in deionized water is added at about 0.42 parts (for a monomer to activator molar ratio of about 200:1) and mixed at about 1,000 rpm. About 27.75 parts hexyl methyl methylene malonate monomer is added in bulk and mixing is continued at about 1,000 rpm. After the polymerization reaction is completed, the emulsion is applied to a steel plate and the water is removed by evaporation. The resulting polymer is a pressure sensitive adhesive and possess representative tack as a result of the polymer. When a crosslinker is added and the PSA material is adhered to steel panel, substantially no polymer is transferred off of the steel panel when a second substrate is applied and removed. The PSA material has good stability after 5 freeze/thaw cycles.

Examples 63 through 88 are polymers prepared using solution polymerization processes as described in U.S. patent application Ser. No. 14/810,741 filed on Jul. 28, 2015, (see e.g., paragraphs 96 through 124 and tables 1-5, incorporated herein by reference). The 1,1-disubstituted alkene compounds employed herein are high purity monomers, having a purity of 97 weight percent or more. The monomers either have only trace impurities and are thus stable from polymerization (anionic or free radical polymerization) or are provided with a sufficient stabilizer package (e.g., about 10 ppm methanesulfonic acid and 100 ppm mono methyl ether hydroquinone) to prevent polymerization prior to the solution polymerization initiated for example by an activator. Unless otherwise specified, the reaction time for the polymerization reaction is about 1 hour or less.

Example 63. Fenchyl-methyl methylene malonate (F3M) is polymerized in solution. The solvent is tetrahydrofuran. A round bottom flask is charged with about 9.0 of tetrahydrofuran and about 1.0 g of the fenchyl-methyl methylene malonate. The mixture is stirred with a magnetic stirrer for about 5 minutes. Tetramethyl guanidine (TMG) is then added to the flask to activate the polymerization reaction. The molar ratio of monomer (F3M) to activator (TMG) is about 1000 (i.e., 1000:1). The polymerization reaction is continued for about 1 hour at a temperature of about 23° C. The polymer is using gel permeation chromatography (GPC) and Differential Scanning Calorimetry (DSC). NMR spectroscopy at the end of the reaction shows no measurable presence of residual monomer. The GPC indicates that the polymer has a first peak in molecular weight at about 2000 and a second peak in molecular weight at about 60,000. The polymer has a polydispersity index of about 1.43. The glass transition temperature of the polymer is about 151° C. In the homopolymerization of fenchyl-methyl methylene malonate, by varying the reaction conditions, the purity of the monomer, the activator concentration and the reaction temperature, the molecular weight distribution of the polymer may be varied between about 1 to 8 and glass transition of the polymer may be increased to be as high as about 190° C. (e.g., when weight average molecular weight is high).

Example 64 is prepared according to the method of Example 63, except the monomer is p-menthyl methyl methylene malonate (4M). The resulting polymer has a glass transition temperature of about 126° C. The number average molecular weight is about 40,000. The homopolymerization of p-menthyl methyl methylene malonate may result in polymer having a glass transition temperature of up to about 145° C. (e.g., by employing process conditions that result in higher weight average molecular weight).

Example 65 is a polymer of diethyl methylene malonate prepared in solution. The molar ratio of monomer (DEMM) to activator (TMG) is about 2000:1. After a 1 hour reaction time, the polymerization is terminated by adding about 0.2 ml of trifluoroacetic acid. The molecular weight distribution of the resulting polymer is measured using gel permeation chromatography and the results are shown in Table 8.

Example 66 is prepared according to the method of preparing Example 65, except the amount of the activator is reduced to about 36 microliters, corresponding to a molar ratio of monomer to activator of about 4000:1. Example 67 is prepared according to the method of preparing Example 65, except the mount of the activator is reduced to about 18 microliters, corresponding to a molar ratio of monomer to activator of about 8000:1. Example 68 is prepared according to the method of preparing Example 65, except the mount of the activator is reduced to about 9 microliters, corresponding to a molar ratio of monomer to activator of about 16000:1. Example 69 is prepared according to the method of preparing Example 65, except the mount of the activator is reduced to about 4.5 microliters, corresponding to a molar ratio of monomer to activator of about 32000:1.

Example 70. Example 70 is prepared by anionic solution polymerization of a 1,1-disubstituted alkene using potassium benzoate and 0.428 g of a crown ether (18-crown 6) in 10 mL of dichloromethane. The molar ratio of potassium benzoate to the crown ether is about 1:2. It is believed that crown ethers may assist in solubilizing the potassium benzoate in DCM. The polymer has a weight average molecular weight of about 405,700 and a number average molecular weight of about 198,000.

Example 71 is prepared by polymerizing diethyl methylene malonate at low temperature. The polymerization is performed at about −78° C. in a Schlenk flask apparatus. The solvent, tetrahydrofuran. The activator is secondary butyl lithium and is provided as a 1.5 M solution in cyclohexane. The reaction temperature is maintained using a dry ice/acetone freezing mixture. The molar ratio of monomer to activator of about 1000:1. The reaction is continued for about 20 minutes and then terminated by adding methanol and trifluoroacetic acid. Aliquots are removed at about 2 minutes, 6 minutes, 10 minutes, and 20 minutes polymerization time. The molecular weight distribution of each aliquot is measured using gel permeation chromatography. The results are given in Table 9.

TABLE 9

|  | Example 71 2 minutes | Example 71 6 minutes | Example 71 10 minutes | Example 71 20 minutes |
| --- | --- | --- | --- | --- |
| Mn, daltons | 12,750 | 20,980 | 36,940 | 41,280 |
| Polydispersity Index | 2.2 | 1.8 | 1.2 | 1.2 |

Example 72. The anionic polymerization of 1,1-disubstituted alkenes may be characterized as a living polymerization. In example 72, the process of Example 71 is repeated except the amount of diethyl methylene malonate initially added to the tetrahydrofuran solvent is about 0.25 g. During the polymerization reaction, a small aliquot is removed every 2 minutes and an additional 0.25 g of the monomer is added to the reaction flask. The process is continued for about 10 minutes, when the polymer begins to precipitate out of the solvent. The amount of activator employed is selected so that the molar ratio of the amount of monomer added in the first injection (i.e., 0.25 g) to the activator is about 1000:1. The molecular weight, measured by gel permeation chromatography increases nearly linearly:

| Time (min) | 0 | 4 | 6 | 8 | 10 |
| --- | --- | --- | --- | --- | --- |
| Mn (daltons) | 0 | 48,000 | 75,000 | 100,000 | 130,000 |

Example 73 is prepared the same as Example 72 except the amount of the activator is increased so that the molar ratio of total monomer to activator is about 100:1. Again, the polymer continues to grow with each additional charge of monomer:

| Time (min) | 2 | 4 | 6 | 8 | 10 |
| --- | --- | --- | --- | --- | --- |
| Mn (daltons) | 8,000 | 22,000 | 41,000 | 58,000 | 81,000 |

TABLE 8

Effects of activator concentration on molecular weight distribution

|  | Example 65 | Example 66 | Example 67 | Example 68 | Example 69 |
| --- | --- | --- | --- | --- | --- |
| DEMM, g | 2.0 | 2.0 | 2.0 | 2.0 | 2.0 |
| THF, g | 18.0 | 18.0 | 18.0 | 18.0 | 18.0 |
| 1% TMG in methylene chloride, μl | 75 | 35.5 | 18 | 9 | 4.5 |
| DEMM:TMG | 2000:1 | 4000:1 | 8000:1 | 16000:1 | 32000:1 |
| Mn (daltons) | 49,000 | 55,000 | 96,000 | 339,000 | 1,080,000 |
| Mw (daltons) | 259,000 | 252,000 | 334,000 | 642,000 | 2,068,000 |
| PDI = Mw/Mn | 5.4 | 4.6 | 3.5 | 1.9 | 1.9 |

Example 74 is a random copolymer prepared using solution polymerization. The method used for Example 65 is used with the following changes: (1) the 2 g of DEMM was replaced with 1 g of (P3M) and 1 g of (H3M); and (2) the amount of the 1 percent TMG activator solution is adjusted so that the molar ratio of the total monomer to the activator is about 1000:1. The polymerization reaction is at about 23° C. The polymer is characterized using gel permeation chromatography and differential scanning calorimetry. The resulting polymer is a random copolymer having a single glass transition temperature of about 27.5° C. The number average molecular weight is about 7,104 daltons, and the weight average molecular weight is about 16,343 daltons, resulting in a polydispersity index, PDI, of about 2.3.

Example 75, 76, and 77 are random copolymers including a first monomer that is a 1,1-disubstituted alkene monomer and a second monomer that is a second 1,1-disubstituted alkene monomer. Example 75, 76, and 77 are prepared using the method of Example 74, except (1) the amount of tetrahydrofuran is about 9 g, and (2) the monomers are replaced with hexyl methyl methylene malonate (HM3) and diethyl methylene malonate (DEMM) with a ratio of HM3 to DEMM of 75:25, 50:50, and 25:75, respectively, and a total of 1 g of monomer. The polymer is characterized by differential scanning calorimetry.

Example 78, is an homopolymer prepared according to the method of Example 75, except the monomer is 1 g of hexyl methyl methylene malonate monomer. The results for examples 75, 76, 77, and 78 are shown in Table 10. These examples each have a single glass transition temperature indicating that 75, 76 and 77 are random copolymers.

TABLE 10

Random Copolymers of hexyl methyl methylene malonate (H3M) and diethyl methylene malonate (DEMM).

|  | Example 78 (homopolymer) | Example 75 | Example 76 | Example 77 |
|---|---|---|---|---|
| H3M, g | 1.0 | 0.25 | 0.5 | 0.5 |
| DEMM, g | 0.0 | 0.25 | 0.25 | 0.5 |
| Mn (daltons) | 33,400 | 39,300 | 48,130 | 160,800 |
| Glass transition temp, ° C. | −19.7° C. | 6.6° C. | −0.4° C. | −34.6° C. |
| Conversion of monomer to polymer | ≈100% | ≈100% | ≈100% | ≈100% |

Example 79 is a block copolymer having four polymer blocks including 2 polymer blocks (A blocks) of a first homopolymer and 2 polymer blocks (B blocks) of a second homopolymer. The block copolymer has the structure: A-B-A-B, where each A and B is a polymer block. Block A consists of 2-pheylpropyl methyl methylene malonate. Block B consists of hexyl methyl methylene malonate. A Schlenk flask is passivated with an acid solution, rinsed with methylene chloride, and dried in an oven. About 18 g of tetrahydrofuran is placed in the Schlenk flask. About 0.25 g of monomer A is then added to the flask. The flask is then capped with a rubber septa and submerged halfway in a bath of acetone and dry ice having a temperature of about −78° C. Vacuum was pulled on the flask and then allowed to back fill with nitrogen. The vacuum/nitrogen back fill is repeated at least 3 times. The solution is mixed using a PTFE coated magnetic stir bar. Using a gas-tight microliter syringe, sec-butyllithium is added as an activator. The amount of the activator is chosen so that the molar ratio of the initial monomer to the activator is about 1000:1. After reacting for about 5 minutes, a small aliquot is removed. This aliquot is quenched with trifluoroacetic acid and the molecular weight distribution of the aliquot is measured using gel permeation chromatography. The aliquot is also characterized using NMR spectroscopy. The polymerization is then continued by injecting about 0.25 g of monomer B into the flask using a syringe and reacting for about 5 minutes. A second aliquot is then removed from the flask before adding a third amount of monomer (0.25 g of monomer A) into the flask using a syringe and reacting for about 5 minutes. A third aliquot is then removed from the flask before adding a fourth amount of monomer (0.25 g of monomer B) into the flask using a syringe and reacting for about 5 minutes. A fourth aliquot is then removed. Each aliquot is treated as the first aliquot (i.e., quenched and then characterized by GPC and NMR). The results of each aliquot are shown in Table 11. The final block copolymer is isolated and characterized using differential scanning calorimetry.

TABLE 11

Properties of Example 79 (block copolymer sample at intermediate stages)

|  | Example 79 $1^{st}$ aliquot | Example 79 $2^{nd}$ aliquot | Example 79 $3^{rd}$ aliquot | Example 79 $4^{th}$ aliquot |
|---|---|---|---|---|
| Monomer A, g | 0.25 | 0.25 | 0.5 | 0.5 |
| Monomer B, g |  | 0.25 | 0.25 | 0.5 |
| Mn, daltons | 28,156 | 41,147 | 59,243 | 67,400 |
| Polydispersity index | 1.06 | 1.07 | 1.06 | 1.07 |
| Conversion of monomer to polymer | ≈100% | ≈100% | ≈100% | ≈100% |

Example 80 is prepared according to the method of Example 69 using tetrahydrofuran as the solvent. The resulting polymer has a number average molecular weight of about 2,000,000 daltons. Example 81 is prepared according to the method of Example 80, except the solvent is heptane. The resulting polymer has a number average molecular weight of about 500,000 daltons. Example 82 is prepared according to the method of Example 80, except the solvent is toluene. The resulting polymer has a number average molecular weight of about 200,000 daltons. Example 83 is prepared according to the method of Example 80, except the solvent is dimethoxy ethane. The resulting polymer has a number average molecular weight of about 700,000 daltons. Example 84 is prepared according to the method of Example 80, except the solvent is dichloromethane. The resulting polymer has a number average molecular weight of about 150,000 daltons.

Example 85 and Example 86 are homopolymers prepared using the method of Example 63, except the monomer is p-menthyl methyl methylene malonate (4M) and the molar ratio of monomer to activator is about 100:1 for Example 85 and about 1000:1 for Example 86. The monomer employed in Example 85 has a purity of about 94.1 weight percent and the monomer employed in Example 86 has a purity of about 98.23 weight percent. Example 85 has a number average molecular weight of about 6,700 daltons, a weight average molecular weight of about 17,400 daltons, a polydispersity index of about 2.60 and a glass transition temperature of about 83° C. Example 86 has a number average molecular weight of about 1,451,800 daltons, a weight average molecular of about 2,239,300 daltons, a polydispersity index of about 1.62, and a glass transition temperature of about 145° C.

Example 87 and Example 88 are homopolymers prepared using the method of Example 63, except the monomer is fenchyl methyl methylene malonate (F3M) and the molar ratio of monomer to activator is about 100:1. The monomer employed in example 87 has a purity of about 92.8 weight percent and the monomer employed in example 88 has a purity of about 98.6 weight percent. Example 87 has a weight average molecular weight of about 40,300 daltons and a glass transition temperature of about 136° C. Example 88 has a weight average molecular of about 290,800 daltons and a glass transition temperature of 190° C.

Example 89 is prepared with by polymerizing diethyl methylene malonate with a multifunctional initiator, JEFFAMINE 403. A representative structure of JEFFAMINE 403 is shown in FIG. 9. The viscosity of the resultant polymer formed in solution is higher than that observed for poly(diethyl methylene malonate) polymerized with similar amount of TMG initiator (which has only one initiation site). Example 89 is representative of branching in the polymer. Example 89 could not be filtered for use in a GPC. It is believed that this is the result of a high degree of branching.

Figure 10:
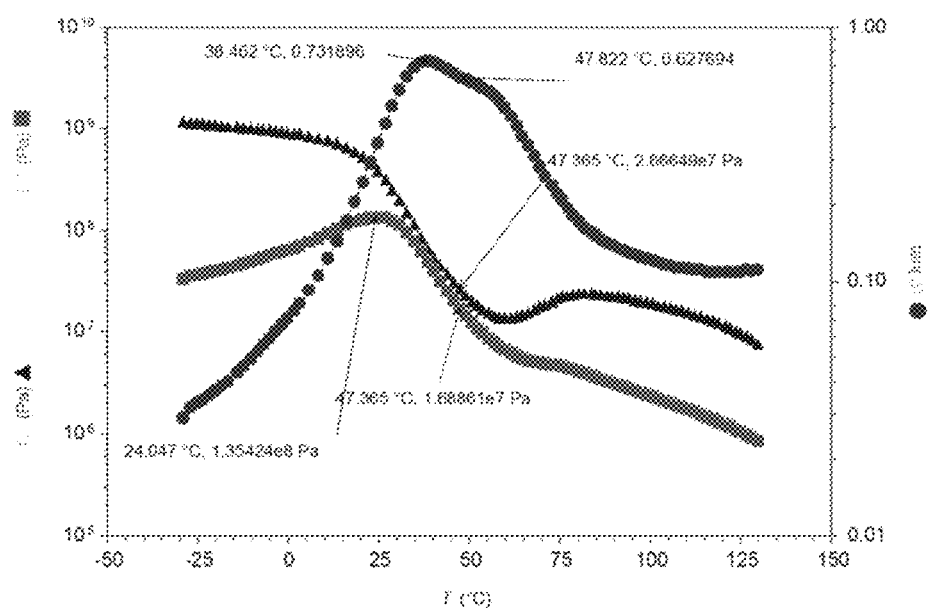
FIG. 10 Shows the dynamical mechanical anlaysis (DMA) of homopolymer of diethyl methylene malonate made in a kilogram scale reactor.

Example 90 is prepared in a kilogram scale reactor by homopolymerizing diethyl methylene malonate. The resultant polymer is cleaned up of any residual monomer by precipitation in methanol. The polymer is then ground up and compression molded into bars for testing using dynamic mechanic analysis. The dynamic mechanical analysis (DMA) for Example 90 is shown in FIG. 10.

Examples LS-1, LS-2, LS-3, and LS-4 are lap shear strength samples prepared by applying a single monomer to a window glass substrate and curing/polymerizing for 24 hours at room temperature. The monomer for Examples LS-1, LS-2, LS-3, and LS-4 are diethyl methylene malonate, dimethyl methylene malonate, methoxyethyl methylene malonate, and hexyl methyl methylene malonate, respectively. The lap shear strength is measured generally according to ASTM D1002 (with the shear strength measured on an Instron at a rate of 50 mm/min). The resulting polymers are homopolymers. Specimen are also tested to determine the setting time at which the polymerization/adhesion is sufficient for supporting a 4.54 kg weight. The results are summarized in the Table below:

| Monomer | EXAMPLE LS-1 | EXAMPLE LS-2 | EXAMPLE LS-3 | EXAMPLE LS-4 |
|---|---|---|---|---|
| diethyl methylene malonate, wt. % | 100 | | | |
| dimethyl methylene malonate, wt. % | | 100 | | |
| methoxyethyl methylene malonate, wt. % | | | 100 | |
| hexyl methyl methylene malonate, wt. % | | | | 100 |
| Test results | | | | |
| Lap shear strength, after 24 hours, zero gap, MPa | 1.0 | 1.3 | 2.9 | 0.6 |
| Failure mode | Adhesive | Adhesive | Substrate + Adhesive | Tacky/Wet |
| Setting rate (Slow; Moderate; Fast) | Fast | Fast | Moderate | Slow |

Examples LS-5, LS-6, LS-7, and LS-8 are lap shear strength samples prepared with mixtures of a generally fast setting monomer (e.g., diethyl methylene malonate or dimethyl methylene malonate) and a slower setting, higher performance monomer (e.g., hexyl methyl methylene malonate or ethyl methyl methylene malonate). The testing was performed using the method described for Example LS-1. The results are summarized in the table below:

| Monomer | EXAMPLE LS-5 | EXAMPLE LS-6 | EXAMPLE LS-7 | EXAMPLE LS-8 |
|---|---|---|---|---|
| diethyl methylene malonate, wt. % | 80 | 60 | 70 | |
| dimethyl methylene malonate, wt. % | | | | 70 |
| ethyl methyl methylene malonate, wt. % | | | 30 | 30 |
| hexyl methyl methylene malonate, wt. % | 20 | 40 | | |
| Test results | | | | |
| Lap shear strength, after 24 hours, zero gap, MPa | 1.9 | 2.5 | 3.0 | 2.0 |
| Failure mode | Adhesive | Adhesive | Substrate | Substrate + Adhesive |
| Setting rate (Slow; Moderate; Fast) | Fast | Moderate | Fast | Fast |

Example LS-6 is also tested for durability after curing for 72 hours at room temperature, by placing the cured specimen in boiling water. Example LS-9 prepared using Loctite glass bonder is similarly prepared and cured for 72 hours at room temperature. Example LS-9 failed after about 60-90 minutes in the boiling water. Example LS-6 did not fail, even after 6 hours immersion in the boiling water. The test is stopped after 6 hours. Example LS-6 and LS-9 are tested in a dishwasher environment for 10 cycles using detergent and water having a temperature of about 40° C. After the 10 cycles in the dishwasher environment, Example LS-9 had a lap shear strength of only about 0.6 MPa, and Example LS-6 had a lap shear strength of about 1.4 MPa.

Examples LS-10, LS-11, LS-12, LS-13, LS-14, LS-15, LS-16, LS-17, and LS-18 are prepared on cold rolled steel. The surface of the cold rolled steel is treated with a solution of 0.1 weight percent sodium pyruvate in ethanol. After evaporating the ethanol, the sodium pyruvate remains on the surface and may function as an initiator. The lap shear strength samples are prepared and tested as described in LS-1 with the monomer and monomer mixtures described in the table below. The lap shear strength results are shown in the table. At 72 hour cure, the monomer mixtures result in a copolymer that provides improved lap shear strength compared to either of the monomers when cured alone.

| Monomer | Example LS-10 | Example LS-11 | Example LS-12 | Example LS-13 | Example LS-14 |
|---|---|---|---|---|---|
| diethyl methylene malonate, wt. % | 100 | | 25 | 50 | 75 |
| fenchyl ethyl methylene malonate, wt. % | | 100 | 75 | 50 | 25 |
| Test results | | | | | |
| Lap shear strength, after 24 hours, zero gap, MPa | 8.2 | 0 | 7.3 | 8.5 | 8.4 |
| Lap shear strength, after 72 hours, zero gap, MPa | 7.4 | 5.9 | 13.6 | 11.4 | 9.1 |
| Setting rate (Slow; Moderate; Fast) | Fast | Slow | Moderate | Moderate | Moderate |

| Monomer | Example LS-10 | Example LS-15 | Example LS-16 | Example LS-17 | Example LS-18 |
|---|---|---|---|---|---|
| diethyl methylene malonate, wt. % | 100 | | 25 | 50 | 75 |
| phenylpropyl methylene malonate, wt. % | | 100 | 75 | 50 | 25 |

| | | | Test results | | |
|---|---|---|---|---|---|
| Lap shear strength, after 24 hours, zero gap, MPa | 8.2 | 1.7 | 6.8 | 6.7 | 7.5 |
| Lap shear strength, after 72 hours, zero gap, MPa | 7.4 | 8.4 | 11.4 | 10.2 | 9.7 |
| Setting rate (Slow; Moderate; Fast) | Fast | Slow | Moderate | Moderate | Moderate |

Such performance synergies are also observed in case of other 'reaction on demand' systems e.g. coatings. The typical procedure to prepare coatings with monomer blends is similar to the sodium pyruvate initiated lap shears described above. The initiator solution of choice here is 0.1% sodium benzoate in butyl cellosolve. The initiator solution is drawn down on a cold rolled steel panel using a Meyer rod #10. The solvent is allowed to evaporate by exposing the panel to 80° C. for 5 minutes. The substrate of the steel is coated evenly with sodium benzoate which functions as the initiator in this case. After this a monomer or a blend of monomers is drawn down on the pre-initiated steel substrate using a Meyer Rod #10. The monomer is allowed to cure at room temperature for 24 hours. Examples C1, C2, C3, C4, C5 and C6 are prepared according to this procedure. Features such as cross hatch adhesion, 180° bend flexibility and solvent resistance (number of MEK wipes) are evaluated after full cure. The results for the combination of various monomers are illustrated in the table below.

| | Example C-1 | Example C-2 | Example C-3 | Example C-4 | Example C-5 | Example C-6 |
|---|---|---|---|---|---|---|
| Monomer | | | | | | |
| diethyl methylene malonate, wt. % | 100 | | 80 | 60 | 80 | 80 |
| hexyl methyl methylene malonate wt. % | | 100 | 20 | 40 | | |
| 1,6 hexane diol difunctional DEMM wt. % | | | | | 20 | |
| Benzene dimethanol difunctional DEMM, wt. % | | | | | | 20 |
| Test results | | | | | | |
| Adhesion (Excellent, Good, Poor) | Poor | Tacky | Good | Excellent | Poor | Poor |
| 180° bend flexibility | Not flexible | Flexible | Moderately flexible | Flexible | Not flexible | Not flexible |
| Solvent resistance (Number of MEK wipes) | <10 | <5 | <10 | <5 | 70 | >100 |
| Cure time (Slow; Moderate; Fast) | Fast | Slow | Fast | Moderate | Moderate | Moderate |

The number average molecular weight is generally expected to be highest when using a polar aprotic solvent. Lower number average molecular weights are generally expected to be obtained when using a nonpolar solvent.

REFERENCE SIGNS FROM DRAWINGS

40 About 6.45 ppm on the NMR spectrograph (corresponding to the reactive double bond peak of diethyl methylene malonate)
42 About 0 ppm on the NMR spectrograph—internal reference
50 GPC peak and area of calculation
52 Weight Average Molecular Weight (Mw)
54 Calibration curve (molecular weight v. retention time) based on PMMA standards
56 Lowest molecular weight calibration (200 daltons)
58 GPC Curve

What is claimed is:

1. A copolymer comprising:
   i) from about 2 weight percent to about 98 weight percent of a first monomer; and
   ii) from about 2 weight percent to about 98 weight percent of a second monomer;
   wherein the first monomer is one or more 1,1-disubstituted alkene monomers and the second monomer includes a styrene, a butadiene, an acrylonitrile, a different 1,1-disubstituted alkene monomer or any combination thereof, wherein when the second monomer is a different 1,1-disubstituted alkene monomer, the first monomer has a structure such that homopolymers of the first monomer have a Tg of about 25° C. or more and the second monomer that is the different 1,1-disubstituted alkene monomer has a structure such that homopolymers of the second monomer have a Tg of about 15° C. or less.

2. The copolymer of claim 1, wherein the polymer is a star polymer having 3 or more arms.

3. The copolymer of claim 1, wherein the copolymer has a linear backbone with long chain branching distributed along the backbone.

4. The copolymer of claim 1, wherein the copolymer includes about 0.002 weight percent to about 2 weight percent of a multifunctional monomer.

5. The polymer of claim 1, wherein the polymer forms a block copolymer.

6. The polymer of claim 1, wherein the polymer is a star polymer having 5 or more arms.

7. The polymer of claim 1, wherein the Tg of the homopolymer of the first polymer is about 35° C. or more.

8. The copolymer of claim 1 including about 50 weight percent or more of the first monomer, wherein the polymer has long chain branching, wherein the polymer has one or any combination of the following characteristics:
   i) a polydispersity of about 3 or less; or
   ii) a weight average molecular weight of about 50,000 or more; or
   iii) is in the form of solid particles.

9. A copolymer comprising:
   i) from about 2 weight percent to about 98 weight percent of a first monomer; and
   ii) from about 2 weight percent to about 98 weight percent of a second monomer;
   wherein the first monomer is one or more 1,1-disubstituted alkene monomers and the second monomer includes one or more acrylates, one or more methacrylates, a styrene, a butadiene, an acrylonitrile, a different 1,1-disubstituted alkene monomer or any combination thereof, wherein the copolymer has a polydispersity of about 2.3 or less and when the second monomer is a different 1,1-disubstituted alkene monomer, the first monomer has a structure such that homopolymers of the first monomer have a Tg of about 25° C. or more and the second monomer that is the different 1,1-disubstituted alkene monomer has a structure such that homopolymers of the second monomer have a Tg of about 15° C. or less.

10. The copolymer of claim 9, wherein the copolymer is a block copolymer.

11. The copolymer of claim 9, wherein the copolymer has a linear backbone with long chain branching distributed along the backbone.

12. The copolymer of claim 9, wherein the copolymer includes about 0.002 weight percent to about 2 weight percent of a multifunctional monomer.

* * * * *